(12) United States Patent
Miller et al.

(10) Patent No.: US 10,772,492 B2
(45) Date of Patent: Sep. 15, 2020

(54) METHODS AND APPARATUS FOR EFFICIENT PURGING

(71) Applicant: INTUITIVE SURGICAL OPERATIONS, INC., Sunnyvale, CA (US)

(72) Inventors: David Miller, Boulder, CO (US); Vahid Saadat, Atherton, CA (US); Zachary J. Malchano, San Francisco, CA (US); Ruey-Feng Peh, Singapore (SG); Aseem K. Thakur, Sunnyvale, CA (US); Christopher A. Rothe, San Mateo, CA (US); Edmund Tam, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 16/457,806

(22) Filed: Jun. 28, 2019

(65) Prior Publication Data

US 2020/0069166 A1   Mar. 5, 2020

Related U.S. Application Data

(60) Division of application No. 15/350,796, filed on Nov. 14, 2016, now Pat. No. 10,368,729, which is a
(Continued)

(51) Int. Cl.
*A61B 1/00* (2006.01)
*A61B 1/04* (2006.01)
(Continued)

(52) U.S. Cl.
CPC ............ *A61B 1/126* (2013.01); *A61B 1/0008* (2013.01); *A61B 1/00082* (2013.01);
(Continued)

(58) Field of Classification Search
CPC ...... A61B 18/1492; A61B 2017/00247; A61B 2017/22051; A61B 2018/00065;
(Continued)

(56) References Cited

U.S. PATENT DOCUMENTS

| 623,022 A | 4/1899 | Johnson |
|---|---|---|
| 2,305,462 A | 12/1942 | Wolf |

(Continued)

FOREIGN PATENT DOCUMENTS

| DE | 2853466 A1 | 6/1979 |
|---|---|---|
| DE | 10028155 A1 | 12/2000 |

(Continued)

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.

(Continued)

*Primary Examiner* — Alexandra L Newton
(74) *Attorney, Agent, or Firm* — Haynes and Boone, LLP

(57) ABSTRACT

A method of inhibiting flow of a purging fluid from a device comprises positioning an imaging hood in proximity to a tissue region to be visualized. The imaging hood includes a distal membrane which defines a main aperture. The imaging hood and the distal membrane define an open area. The method also comprises introducing the purging fluid into a proximal portion of the open area. The proximal portion is bounded by a proximal membrane including a plurality of apertures. The method also comprises pressurizing the proximal membrane with the purging fluid to a partially extended state in which the purging fluid flows through the plurality of apertures and through the main aperture. The method also comprises pressurizing the proximal membrane with the purging fluid to a blocking extended state in which (Continued)

the proximal membrane obstructs the main aperture to block the flow of the purging fluid through the main aperture.

10 Claims, 14 Drawing Sheets

Related U.S. Application Data continuation of application No. 12/499,681, filed on Jul. 8, 2009, now Pat. No. 9,510,732, which is a continuation-in-part of application No. 11/259,498, filed on Oct. 25, 2005, now Pat. No. 7,860,555.

(60) Provisional application No. 61/079,414, filed on Jul. 9, 2008, provisional application No. 60/649,246, filed on Feb. 2, 2005.

(51) Int. Cl.
  *A61B 1/12* (2006.01)
  *A61B 1/05* (2006.01)
(52) U.S. Cl.
  CPC ...... *A61B 1/00089* (2013.01); *A61B 1/00165* (2013.01); *A61B 1/051* (2013.01)
(58) Field of Classification Search
  CPC ........... A61B 2018/00351; A61B 2018/00392; A61M 2025/1052; A61M 2025/1081; A61M 25/10
  USPC ......... 604/96.01–103.14, 104–109; 606/192, 606/194, 200; 600/104, 109, 115, 127, 600/129, 153, 156, 158, 159
  See application file for complete search history.

(56) References Cited

U.S. PATENT DOCUMENTS

| | | | |
|---|---|---|---|
| 2,453,862 A | | 11/1948 | Salisbury |
| 3,559,651 A | | 2/1971 | David |
| 3,831,587 A | | 8/1974 | Boyd |
| 3,874,388 A | | 4/1975 | King et al. |
| 3,903,877 A | | 9/1975 | Terada |
| 4,175,545 A | | 11/1979 | Termanini |
| 4,326,529 A | | 4/1982 | Doss et al. |
| 4,403,612 A | | 9/1983 | Fogarty |
| 4,445,892 A | | 5/1984 | Hussein et al. |
| 4,470,407 A | | 9/1984 | Hussein |
| 4,517,976 A | | 5/1985 | Murakoshi et al. |
| 4,569,335 A | | 2/1986 | Tsuno |
| 4,576,146 A | | 3/1986 | Kawazoe et al. |
| 4,615,333 A | | 10/1986 | Taguchi |
| 4,619,247 A | | 10/1986 | Inoue et al. |
| 4,676,258 A | | 6/1987 | Inokuchi et al. |
| 4,681,093 A | * | 7/1987 | Ono ................... A61B 1/00082 600/116 |
| 4,709,698 A | | 12/1987 | Johnston et al. |
| 4,710,192 A | * | 12/1987 | Liotta ................... A61B 17/12 604/907 |
| 4,727,418 A | | 2/1988 | Kato et al. |
| 4,772,260 A | | 9/1988 | Heyden |
| 4,784,133 A | | 11/1988 | Mackin |
| 4,838,246 A | | 6/1989 | Hahn et al. |
| 4,848,323 A | | 7/1989 | Marijnissen et al. |
| 4,880,015 A | | 11/1989 | Nierman |
| 4,911,148 A | | 3/1990 | Sosnowski et al. |
| 4,914,521 A | | 4/1990 | Adair |
| 4,943,290 A | | 7/1990 | Rexroth et al. |
| 4,950,285 A | | 8/1990 | Wilk |
| 4,957,484 A | | 9/1990 | Murtfeldt |
| 4,960,411 A | | 10/1990 | Buchbinder |
| 4,961,738 A | * | 10/1990 | Mackin ............... A61B 1/00082 600/116 |
| 4,976,710 A | | 12/1990 | Mackin |
| 4,991,578 A | | 2/1991 | Cohen |
| 4,994,069 A | | 2/1991 | Ritchart et al. |
| 4,998,916 A | | 3/1991 | Hammerslag et al. |
| 4,998,972 A | | 3/1991 | Chin et al. |
| 5,025,778 A | | 6/1991 | Silverstein et al. |
| 5,047,028 A | | 9/1991 | Qian |
| 5,057,106 A | | 10/1991 | Kasevich et al. |
| 5,090,959 A | | 2/1992 | Samson et al. |
| 5,123,428 A | | 6/1992 | Schwarz |
| RE34,002 E | | 7/1992 | Adair |
| 5,156,141 A | | 10/1992 | Krebs et al. |
| 5,171,259 A | | 12/1992 | Inoue |
| 5,197,457 A | | 3/1993 | Adair |
| 5,281,238 A | | 1/1994 | Chin et al. |
| 5,282,827 A | | 2/1994 | Kensey et al. |
| 5,306,234 A | | 4/1994 | Johnson |
| 5,313,934 A | | 5/1994 | Wiita et al. |
| 5,313,943 A | | 5/1994 | Houser et al. |
| 5,330,496 A | | 7/1994 | Alferness |
| 5,334,159 A | | 8/1994 | Turkel |
| 5,334,193 A | | 8/1994 | Nardella |
| 5,336,252 A | | 8/1994 | Cohen |
| 5,339,800 A | | 8/1994 | Wiita et al. |
| 5,345,927 A | | 9/1994 | Bonutti |
| 5,348,554 A | | 9/1994 | Imran et al. |
| 5,353,792 A | | 10/1994 | Luebbers et al. |
| 5,370,647 A | * | 12/1994 | Graber ............. A61B 17/00234 606/127 |
| 5,373,840 A | | 12/1994 | Knighton |
| 5,375,612 A | | 12/1994 | Cottenceau et al. |
| 5,385,146 A | | 1/1995 | Goldreyer |
| 5,385,148 A | | 1/1995 | Lesh et al. |
| 5,391,182 A | | 2/1995 | Chin |
| 5,403,326 A | | 4/1995 | Harrison et al. |
| 5,405,360 A | | 4/1995 | Tovey |
| 5,405,376 A | | 4/1995 | Mulier et al. |
| 5,409,483 A | | 4/1995 | Campbell et al. |
| 5,411,016 A | | 5/1995 | Kume et al. |
| 5,413,104 A | * | 5/1995 | Buijs .................... G01R 33/285 600/423 |
| 5,421,338 A | | 6/1995 | Crowley et al. |
| 5,431,649 A | | 7/1995 | Mulier et al. |
| 5,453,785 A | | 9/1995 | Lenhardt et al. |
| 5,462,521 A | | 10/1995 | Brucker et al. |
| 5,471,515 A | | 11/1995 | Fossum et al. |
| 5,498,230 A | | 3/1996 | Adair |
| 5,505,730 A | | 4/1996 | Edwards |
| 5,515,853 A | | 5/1996 | Smith et al. |
| 5,527,338 A | | 6/1996 | Purdy |
| 5,549,603 A | | 8/1996 | Feiring |
| 5,558,619 A | | 9/1996 | Kami et al. |
| 5,571,088 A | | 11/1996 | Lennox et al. |
| 5,575,756 A | | 11/1996 | Karasawa et al. |
| 5,575,810 A | | 11/1996 | Swanson et al. |
| 5,584,872 A | * | 12/1996 | LaFontaine ........ A61B 18/1485 607/116 |
| 5,591,119 A | | 1/1997 | Adair |
| 5,593,405 A | | 1/1997 | Osypka |
| 5,593,422 A | | 1/1997 | Muijs Van De Moer et al. |
| 5,593,424 A | | 1/1997 | Northrup, III |
| 5,643,282 A | | 7/1997 | Kieturakis |
| 5,653,677 A | | 8/1997 | Okada et al. |
| 5,662,671 A | | 9/1997 | Barbut et al. |
| 5,665,062 A | | 9/1997 | Houser |
| 5,672,153 A | | 9/1997 | Lax et al. |
| 5,676,693 A | | 10/1997 | Lafontaine |
| 5,681,308 A | | 10/1997 | Edwards et al. |
| 5,695,448 A | | 12/1997 | Kimura et al. |
| 5,697,281 A | | 12/1997 | Eggers et al. |
| 5,697,882 A | | 12/1997 | Eggers et al. |
| 5,709,224 A | | 1/1998 | Behl et al. |
| 5,713,907 A | | 2/1998 | Hogendijk et al. |
| 5,713,946 A | | 2/1998 | Ben-Haim |
| 5,716,321 A | | 2/1998 | Kerin et al. |
| 5,716,325 A | | 2/1998 | Bonutti |
| 5,722,403 A | | 3/1998 | McGee et al. |
| 5,725,523 A | * | 3/1998 | Mueller ............. A61B 1/00098 606/15 |
| 5,743,851 A | | 4/1998 | Moll et al. |

(56) References Cited

U.S. PATENT DOCUMENTS

| | | |
|---|---|---|
| 5,746,747 A | 5/1998 | McKeating |
| 5,749,846 A | 5/1998 | Edwards et al. |
| 5,749,889 A | 5/1998 | Bacich et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A * | 10/1998 | Yoon ................ A61B 17/00234 600/207 |
| 5,827,175 A | 10/1998 | Tanaka et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,846,221 A | 12/1998 | Snoke et al. |
| 5,846,239 A * | 12/1998 | Swanson ................ A61N 1/05 606/41 |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | Lafontaine et al. |
| 5,904,651 A | 5/1999 | Swanson et al. |
| 5,908,445 A | 6/1999 | Whayne et al. |
| 5,916,147 A | 6/1999 | Boury |
| 5,925,038 A | 7/1999 | Panescu et al. |
| 5,928,250 A | 7/1999 | Koike et al. |
| 5,929,901 A | 7/1999 | Adair et al. |
| 5,937,614 A | 8/1999 | Watkins et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,980,484 A | 11/1999 | Ressemann et al. |
| 5,985,307 A * | 11/1999 | Hanson ................ A61F 2/06 424/423 |
| 5,986,693 A | 11/1999 | Adair et al. |
| 5,997,571 A | 12/1999 | Farr et al. |
| 6,004,269 A | 12/1999 | Crowley et al. |
| 6,007,521 A | 12/1999 | Bidwell et al. |
| 6,012,457 A | 1/2000 | Lesh |
| 6,013,024 A | 1/2000 | Mitsuda et al. |
| 6,024,740 A | 2/2000 | Lesh et al. |
| 6,027,501 A | 2/2000 | Goble et al. |
| 6,036,685 A * | 3/2000 | Mueller ............ A61B 1/00098 606/15 |
| 6,043,839 A | 3/2000 | Adair et al. |
| 6,047,218 A | 4/2000 | Whayne et al. |
| 6,063,077 A | 5/2000 | Schaer |
| 6,063,081 A | 5/2000 | Mulier et al. |
| 6,068,653 A | 5/2000 | Lafontaine |
| 6,071,279 A | 6/2000 | Whayne et al. |
| 6,071,302 A | 6/2000 | Sinofsky et al. |
| 6,081,740 A | 6/2000 | Gombrich et al. |
| 6,086,528 A | 7/2000 | Adair |
| 6,086,534 A | 7/2000 | Kesten |
| 6,099,498 A | 8/2000 | Addis |
| 6,099,514 A | 8/2000 | Sharkey et al. |
| 6,102,905 A | 8/2000 | Baxter et al. |
| 6,112,123 A | 8/2000 | Kelleher et al. |
| 6,115,626 A | 9/2000 | Whayne et al. |
| 6,123,703 A | 9/2000 | Tu et al. |
| 6,123,718 A | 9/2000 | Tu et al. |
| 6,129,724 A | 10/2000 | Fleischman et al. |
| 6,139,508 A | 10/2000 | Simpson et al. |
| 6,142,993 A | 11/2000 | Whayne et al. |
| 6,152,144 A * | 11/2000 | Lesh ................ A61B 17/0057 128/898 |
| 6,156,350 A | 12/2000 | Constantz |
| 6,159,203 A | 12/2000 | Sinofsky |
| 6,161,543 A | 12/2000 | Cox et al. |
| 6,164,283 A | 12/2000 | Lesh |
| 6,167,297 A | 12/2000 | Benaron |
| 6,168,591 B1 | 1/2001 | Sinofsky |
| 6,168,594 B1 * | 1/2001 | LaFontaine ........ A61B 18/1485 606/41 |
| 6,174,307 B1 | 1/2001 | Daniel et al. |
| 6,178,346 B1 | 1/2001 | Amundson et al. |
| 6,190,381 B1 | 2/2001 | Olsen et al. |
| 6,211,904 B1 | 4/2001 | Adair et al. |
| 6,224,553 B1 | 5/2001 | Nevo |
| 6,231,561 B1 | 5/2001 | Frazier et al. |
| 6,234,995 B1 | 5/2001 | Peacock, III |
| 6,235,044 B1 * | 5/2001 | Root ................ A61B 18/1492 606/200 |
| 6,237,605 B1 | 5/2001 | Vaska et al. |
| 6,238,393 B1 | 5/2001 | Mulier et al. |
| 6,240,312 B1 | 5/2001 | Alfano et al. |
| 6,254,598 B1 | 7/2001 | Edwards et al. |
| 6,258,083 B1 | 7/2001 | Daniel et al. |
| 6,263,224 B1 | 7/2001 | West |
| 6,266,551 B1 | 7/2001 | Osadchy et al. |
| 6,270,492 B1 | 8/2001 | Sinofsky |
| 6,275,255 B1 | 8/2001 | Adair et al. |
| 6,280,450 B1 | 8/2001 | McGuckin, Jr. |
| 6,290,689 B1 | 9/2001 | Delaney et al. |
| 6,306,081 B1 | 10/2001 | Ishikawa et al. |
| 6,310,642 B1 | 10/2001 | Adair et al. |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,777 B1 | 11/2001 | Comben |
| 6,315,778 B1 * | 11/2001 | Gambale ............ A61B 18/1492 606/41 |
| 6,322,536 B1 | 11/2001 | Rosengart et al. |
| 6,325,797 B1 | 12/2001 | Stewart et al. |
| 6,328,727 B1 | 12/2001 | Frazier et al. |
| 6,358,247 B1 | 3/2002 | Altman et al. |
| 6,358,248 B1 | 3/2002 | Mulier et al. |
| 6,375,654 B1 | 4/2002 | McIntyre |
| 6,379,345 B1 | 4/2002 | Constantz |
| 6,383,195 B1 | 5/2002 | Richard |
| 6,385,476 B1 | 5/2002 | Osadchy et al. |
| 6,387,043 B1 | 5/2002 | Yoon |
| 6,387,071 B1 | 5/2002 | Constantz |
| 6,394,096 B1 | 5/2002 | Constantz |
| 6,396,873 B1 | 5/2002 | Goldstein et al. |
| 6,398,780 B1 | 6/2002 | Farley et al. |
| 6,401,719 B1 | 6/2002 | Farley et al. |
| 6,409,722 B1 | 6/2002 | Hoey et al. |
| 6,416,511 B1 | 7/2002 | Lesh et al. |
| 6,419,669 B1 | 7/2002 | Frazier et al. |
| 6,423,051 B1 | 7/2002 | Kaplan et al. |
| 6,423,055 B1 | 7/2002 | Farr et al. |
| 6,423,058 B1 | 7/2002 | Edwards et al. |
| 6,428,536 B2 | 8/2002 | Panescu et al. |
| 6,436,118 B1 | 8/2002 | Kayan |
| 6,440,061 B1 | 8/2002 | Wenner et al. |
| 6,440,119 B1 | 8/2002 | Nakada et al. |
| 6,458,151 B1 | 10/2002 | Saltiel |
| 6,461,327 B1 | 10/2002 | Addis et al. |
| 6,464,697 B1 | 10/2002 | Edwards et al. |
| 6,474,340 B1 | 11/2002 | Vaska et al. |
| 6,475,223 B1 | 11/2002 | Werp et al. |
| 6,478,769 B1 | 11/2002 | Parker |
| 6,482,162 B1 | 11/2002 | Moore |
| 6,484,727 B1 | 11/2002 | Vaska et al. |
| 6,485,489 B2 | 11/2002 | Teirstein et al. |
| 6,488,671 B1 | 12/2002 | Constantz et al. |
| 6,494,902 B2 | 12/2002 | Hoey et al. |
| 6,497,651 B1 | 12/2002 | Kan et al. |
| 6,497,705 B2 | 12/2002 | Comben |
| 6,500,174 B1 | 12/2002 | Maguire et al. |
| 6,502,576 B1 | 1/2003 | Lesh |
| 6,514,249 B1 | 2/2003 | Maguire et al. |

(56) References Cited

U.S. PATENT DOCUMENTS

| | | | |
|---|---|---|---|
| 6,517,533 B1 * | 2/2003 | Swaminathan | A61B 18/0218 600/3 |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 * | 4/2003 | Hassett | A61B 18/1492 606/45 |
| 6,544,195 B2 | 4/2003 | Wilson et al. | |
| 6,547,780 B1 | 4/2003 | Sinofsky | |
| 6,549,800 B1 | 4/2003 | Atalar et al. | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,572,609 B1 | 6/2003 | Farr et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 * | 8/2003 | Sinofsky | A61B 18/24 604/101.02 |
| 6,613,062 B1 | 9/2003 | Leckrone et al. | |
| 6,622,732 B2 | 9/2003 | Constantz | |
| 6,623,900 B1 | 9/2003 | Sinofsky et al. | |
| 6,626,855 B1 | 9/2003 | Weng et al. | |
| 6,626,899 B2 | 9/2003 | Houser et al. | |
| 6,632,171 B2 | 10/2003 | Iddan et al. | |
| 6,635,070 B2 | 10/2003 | Leeflang et al. | |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,663,821 B2 * | 12/2003 | Seward | A61M 39/24 137/859 |
| 6,673,090 B2 | 1/2004 | Root et al. | |
| 6,676,656 B2 | 1/2004 | Sinofsky | |
| 6,679,836 B2 | 1/2004 | Couvillon, Jr. et al. | |
| 6,682,526 B1 * | 1/2004 | Jones | A61B 18/1492 606/32 |
| 6,689,051 B2 | 2/2004 | Nakada et al. | |
| 6,689,128 B2 | 2/2004 | Sliwa et al. | |
| 6,692,430 B2 | 2/2004 | Adler | |
| 6,701,581 B2 | 3/2004 | Senovich et al. | |
| 6,701,931 B2 | 3/2004 | Sliwa et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa et al. | |
| 6,730,063 B2 | 5/2004 | Delaney et al. | |
| 6,736,810 B2 | 5/2004 | Hoey et al. | |
| 6,749,617 B1 | 6/2004 | Palasis et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,770,070 B1 | 8/2004 | Balbierz | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa et al. | |
| 6,849,073 B2 | 2/2005 | Hoey et al. | |
| 6,858,005 B2 | 2/2005 | Ohline et al. | |
| 6,858,026 B2 | 2/2005 | Sliwa et al. | |
| 6,858,905 B2 | 2/2005 | Hsu et al. | |
| 6,863,668 B2 | 3/2005 | Gillespie et al. | |
| 6,866,651 B2 | 3/2005 | Constantz | |
| 6,887,237 B2 | 5/2005 | McGaffigan | |
| 6,892,091 B1 | 5/2005 | Ben-Haim et al. | |
| 6,896,690 B1 | 5/2005 | Lambrecht et al. | |
| 6,899,672 B2 | 5/2005 | Chin et al. | |
| 6,915,154 B1 | 7/2005 | Docherty et al. | |
| 6,916,284 B2 | 7/2005 | Moriyama | |
| 6,916,286 B2 | 7/2005 | Kazakevich | |
| 6,923,805 B1 | 8/2005 | Lafontaine et al. | |
| 6,929,010 B2 | 8/2005 | Vaska et al. | |
| 6,932,809 B2 | 8/2005 | Sinofsky | |
| 6,939,348 B2 | 9/2005 | Malecki et al. | |
| 6,942,657 B2 | 9/2005 | Sinofsky et al. | |
| 6,949,095 B2 | 9/2005 | Vaska et al. | |
| 6,953,457 B2 | 10/2005 | Farr et al. | |
| 6,955,173 B2 | 10/2005 | Lesh | |
| 6,958,069 B2 | 10/2005 | Shipp et al. | |
| 6,962,589 B2 | 11/2005 | Mulier et al. | |
| 6,971,394 B2 | 12/2005 | Sliwa et al. | |
| 6,974,464 B2 | 12/2005 | Quijano et al. | |
| 6,979,290 B2 | 12/2005 | Mourlas et al. | |
| 6,982,740 B2 | 1/2006 | Adair et al. | |
| 6,984,232 B2 | 1/2006 | Vanney et al. | |
| 6,994,094 B2 | 2/2006 | Schwartz | |
| 7,001,329 B2 | 2/2006 | Kobayashi et al. | |
| 7,019,610 B2 | 3/2006 | Creighton et al. | |
| 7,025,746 B2 | 4/2006 | Tal | |
| 7,030,904 B2 | 4/2006 | Adair et al. | |
| 7,041,098 B2 | 5/2006 | Farley et al. | |
| 7,042,487 B2 | 5/2006 | Nakashima | |
| 7,044,135 B2 | 5/2006 | Lesh | |
| 7,052,493 B2 | 5/2006 | Vaska et al. | |
| 7,090,683 B2 | 8/2006 | Brock et al. | |
| 7,118,566 B2 | 10/2006 | Jahns | |
| 7,156,845 B2 | 1/2007 | Mulier et al. | |
| 7,163,534 B2 | 1/2007 | Brucker et al. | |
| 7,166,537 B2 | 1/2007 | Jacobsen et al. | |
| 7,169,144 B2 | 1/2007 | Hoey et al. | |
| 7,179,224 B2 | 2/2007 | Willis | |
| 7,186,214 B2 | 3/2007 | Ness | |
| 7,207,984 B2 | 4/2007 | Farr et al. | |
| 7,217,268 B2 | 5/2007 | Eggers et al. | |
| 7,242,832 B2 | 7/2007 | Carlin et al. | |
| 7,247,155 B2 | 7/2007 | Hoey et al. | |
| 7,261,711 B2 | 8/2007 | Mulier et al. | |
| 7,263,397 B2 | 8/2007 | Hauck et al. | |
| 7,276,061 B2 | 10/2007 | Schaer et al. | |
| 7,309,328 B2 | 12/2007 | Kaplan et al. | |
| 7,322,934 B2 | 1/2008 | Miyake et al. | |
| 7,323,001 B2 | 1/2008 | Clubb et al. | |
| 7,416,552 B2 | 8/2008 | Paul et al. | |
| 7,435,248 B2 | 10/2008 | Taimisto et al. | |
| 7,527,625 B2 | 5/2009 | Knight et al. | |
| 7,534,204 B2 * | 5/2009 | Starksen | A61B 17/00234 600/116 |
| 7,534,294 B1 | 5/2009 | Gaynor et al. | |
| 7,569,052 B2 * | 8/2009 | Phan | A61B 18/1492 606/35 |
| 7,569,952 B1 | 8/2009 | Bono et al. | |
| 7,736,347 B2 | 6/2010 | Kaplan et al. | |
| 7,758,499 B2 | 7/2010 | Adler | |
| 7,860,555 B2 * | 12/2010 | Saadat | A61B 1/0008 600/476 |
| 7,860,556 B2 | 12/2010 | Saadat | |
| 7,918,787 B2 | 4/2011 | Saadat | |
| 7,919,610 B2 | 4/2011 | Serebriiskii et al. | |
| 7,930,016 B1 | 4/2011 | Saadat | |
| 8,050,746 B2 | 11/2011 | Saadat et al. | |
| 8,078,266 B2 * | 12/2011 | Saadat | A61B 1/0008 600/476 |
| 8,131,350 B2 * | 3/2012 | Saadat | A61B 1/00089 600/101 |
| 8,137,333 B2 | 3/2012 | Saadat et al. | |
| 8,221,310 B2 | 7/2012 | Saadat et al. | |
| 8,235,985 B2 | 8/2012 | Saadat et al. | |
| 8,333,012 B2 | 12/2012 | Rothe et al. | |
| 8,417,321 B2 | 4/2013 | Saadat et al. | |
| 8,419,613 B2 | 4/2013 | Saadat et al. | |
| 8,475,361 B2 | 7/2013 | Barlow et al. | |
| 8,657,805 B2 | 2/2014 | Peh et al. | |

(56) References Cited

U.S. PATENT DOCUMENTS

| | | | |
|---|---|---|---|
| 8,758,229 B2 | 6/2014 | Saadat et al. | |
| 8,814,845 B2 | 8/2014 | Saadat et al. | |
| 8,906,007 B2* | 12/2014 | Bonn | A61B 18/1815 606/33 |
| 8,934,962 B2 | 1/2015 | Saadat et al. | |
| 9,055,906 B2 | 6/2015 | Saadat et al. | |
| 9,192,287 B2 | 11/2015 | Saadat et al. | |
| 9,226,648 B2 | 1/2016 | Saadat et al. | |
| 9,332,893 B2 | 5/2016 | Saadat et al. | |
| 9,510,732 B2 | 12/2016 | Miller et al. | |
| 9,526,401 B2 | 12/2016 | Saadat et al. | |
| 10,004,388 B2 | 6/2018 | Saadat et al. | |
| 10,064,540 B2 | 9/2018 | Saadat et al. | |
| 10,070,772 B2 | 9/2018 | Peh et al. | |
| 10,092,172 B2 | 10/2018 | Peh et al. | |
| 10,278,588 B2 | 5/2019 | Saadat et al. | |
| 10,368,729 B2 | 8/2019 | Miller et al. | |
| 10,390,685 B2 | 8/2019 | Saadat et al. | |
| 10,470,643 B2 | 11/2019 | Saadat et al. | |
| 2001/0005789 A1* | 6/2001 | Root | A61B 18/1492 606/200 |
| 2001/0020126 A1 | 9/2001 | Swanson et al. | |
| 2001/0039416 A1 | 11/2001 | Moorman et al. | |
| 2001/0047136 A1 | 11/2001 | Domanik et al. | |
| 2001/0047184 A1 | 11/2001 | Connors | |
| 2002/0004644 A1 | 1/2002 | Koblish | |
| 2002/0026145 A1 | 2/2002 | Bagaoisan et al. | |
| 2002/0035311 A1 | 3/2002 | Ouchi | |
| 2002/0054852 A1 | 5/2002 | Cate | |
| 2002/0065455 A1 | 5/2002 | Ben-Haim et al. | |
| 2002/0077594 A1* | 6/2002 | Chien | A61M 25/10 604/103.02 |
| 2002/0077642 A1 | 6/2002 | Patel et al. | |
| 2002/0087169 A1 | 7/2002 | Brock et al. | |
| 2002/0091304 A1 | 7/2002 | Ogura et al. | |
| 2002/0138088 A1* | 9/2002 | Nash | A61B 17/32037 606/159 |
| 2002/0161377 A1 | 10/2002 | Rabkin et al. | |
| 2002/0165598 A1 | 11/2002 | Wahr et al. | |
| 2002/0169377 A1 | 11/2002 | Khairkhahan et al. | |
| 2003/0009085 A1 | 1/2003 | Arai et al. | |
| 2003/0014010 A1 | 1/2003 | Carpenter et al. | |
| 2003/0018358 A1 | 1/2003 | Saadat | |
| 2003/0035156 A1 | 2/2003 | Cooper | |
| 2003/0036698 A1 | 2/2003 | Kohler et al. | |
| 2003/0065267 A1 | 4/2003 | Smith | |
| 2003/0069593 A1 | 4/2003 | Tremulis et al. | |
| 2003/0120142 A1 | 6/2003 | Dubuc et al. | |
| 2003/0130572 A1 | 7/2003 | Phan et al. | |
| 2003/0144657 A1 | 7/2003 | Bowe et al. | |
| 2003/0171741 A1 | 9/2003 | Ziebol et al. | |
| 2003/0181939 A1* | 9/2003 | Bonutti | A61B 17/0218 606/192 |
| 2003/0208222 A1 | 11/2003 | Zadno-Azizi | |
| 2003/0212394 A1 | 11/2003 | Pearson et al. | |
| 2003/0220574 A1 | 11/2003 | Markus et al. | |
| 2003/0222325 A1 | 12/2003 | Jacobsen et al. | |
| 2003/0236493 A1 | 12/2003 | Mauch | |
| 2004/0006333 A1* | 1/2004 | Arnold | A61B 18/24 606/15 |
| 2004/0044350 A1 | 3/2004 | Martin et al. | |
| 2004/0049211 A1 | 3/2004 | Tremulis et al. | |
| 2004/0054335 A1 | 3/2004 | Lesh et al. | |
| 2004/0054389 A1 | 3/2004 | Osypka | |
| 2004/0082833 A1 | 4/2004 | Adler et al. | |
| 2004/0097788 A1* | 5/2004 | Mourlas | A61B 1/00082 600/116 |
| 2004/0097792 A1 | 5/2004 | Moll et al. | |
| 2004/0098031 A1 | 5/2004 | Van Der Burg et al. | |
| 2004/0117032 A1 | 6/2004 | Roth | |
| 2004/0133113 A1 | 7/2004 | Krishnan | |
| 2004/0138707 A1 | 7/2004 | Greenhalgh | |
| 2004/0147806 A1 | 7/2004 | Adler | |
| 2004/0147911 A1 | 7/2004 | Sinofsky | |
| 2004/0147912 A1 | 7/2004 | Sinofsky | |
| 2004/0147913 A1 | 7/2004 | Sinofsky | |
| 2004/0158143 A1 | 8/2004 | Flaherty et al. | |
| 2004/0158289 A1 | 8/2004 | Girouard et al. | |
| 2004/0165766 A1 | 8/2004 | Goto | |
| 2004/0167503 A1 | 8/2004 | Sinofsky | |
| 2004/0181237 A1* | 9/2004 | Forde | A61B 17/12122 606/108 |
| 2004/0199052 A1 | 10/2004 | Banik et al. | |
| 2004/0210111 A1 | 10/2004 | Okada | |
| 2004/0210239 A1 | 10/2004 | Nash et al. | |
| 2004/0215180 A1 | 10/2004 | Starkebaum et al. | |
| 2004/0220471 A1 | 11/2004 | Schwartz | |
| 2004/0230131 A1 | 11/2004 | Kassab et al. | |
| 2004/0248837 A1 | 12/2004 | Raz et al. | |
| 2004/0249367 A1 | 12/2004 | Saadat et al. | |
| 2004/0254523 A1* | 12/2004 | Fitzgerald | A61M 1/3615 604/21 |
| 2004/0260182 A1 | 12/2004 | Zuluaga et al. | |
| 2005/0004597 A1* | 1/2005 | McGuckin, Jr. | A61F 2/013 606/200 |
| 2005/0014995 A1 | 1/2005 | Amundson et al. | |
| 2005/0015048 A1* | 1/2005 | Chiu | A61M 25/10 604/101.04 |
| 2005/0020914 A1 | 1/2005 | Amundson et al. | |
| 2005/0027163 A1 | 2/2005 | Chin et al. | |
| 2005/0038419 A9 | 2/2005 | Arnold et al. | |
| 2005/0059862 A1* | 3/2005 | Phan | A61B 1/00165 600/176 |
| 2005/0059954 A1* | 3/2005 | Constantz | A61B 17/11 604/500 |
| 2005/0059965 A1 | 3/2005 | Eberl et al. | |
| 2005/0059984 A1 | 3/2005 | Chanduszko et al. | |
| 2005/0065504 A1* | 3/2005 | Melsky | A61B 18/22 606/16 |
| 2005/0090818 A1 | 4/2005 | Pike et al. | |
| 2005/0096502 A1 | 5/2005 | Khalili | |
| 2005/0096643 A1 | 5/2005 | Brucker et al. | |
| 2005/0101984 A1 | 5/2005 | Chanduszko et al. | |
| 2005/0107736 A1 | 5/2005 | Landman et al. | |
| 2005/0119523 A1* | 6/2005 | Starksen | A61B 17/00234 600/109 |
| 2005/0124969 A1 | 6/2005 | Fitzgerald et al. | |
| 2005/0131401 A1* | 6/2005 | Malecki | A61B 17/0057 606/27 |
| 2005/0154252 A1 | 7/2005 | Sharkey et al. | |
| 2005/0159702 A1 | 7/2005 | Sekiguchi et al. | |
| 2005/0165272 A1 | 7/2005 | Okada et al. | |
| 2005/0165279 A1 | 7/2005 | Adler et al. | |
| 2005/0165391 A1 | 7/2005 | Maguire et al. | |
| 2005/0165466 A1 | 7/2005 | Morris et al. | |
| 2005/0197530 A1* | 9/2005 | Wallace | A61B 1/00082 600/116 |
| 2005/0197623 A1 | 9/2005 | Leeflang et al. | |
| 2005/0215895 A1 | 9/2005 | Popp et al. | |
| 2005/0222554 A1 | 10/2005 | Wallace et al. | |
| 2005/0222557 A1 | 10/2005 | Baxter et al. | |
| 2005/0222558 A1 | 10/2005 | Baxter et al. | |
| 2005/0228452 A1 | 10/2005 | Mourlas et al. | |
| 2005/0234436 A1 | 10/2005 | Baxter et al. | |
| 2005/0234437 A1 | 10/2005 | Baxter et al. | |
| 2005/0267328 A1 | 12/2005 | Blumzvig et al. | |
| 2006/0009715 A1 | 1/2006 | Khairkhahan et al. | |
| 2006/0009737 A1 | 1/2006 | Whiting et al. | |
| 2006/0015096 A1 | 1/2006 | Hauck et al. | |
| 2006/0022234 A1 | 2/2006 | Adair et al. | |
| 2006/0025651 A1 | 2/2006 | Adler et al. | |
| 2006/0025787 A1 | 2/2006 | Morales et al. | |
| 2006/0069303 A1 | 3/2006 | Couvillon, Jr. | |
| 2006/0074398 A1 | 4/2006 | Whiting et al. | |
| 2006/0084839 A1* | 4/2006 | Mourlas | A61B 1/00082 600/116 |
| 2006/0084945 A1 | 4/2006 | Moll et al. | |
| 2006/0089637 A1 | 4/2006 | Werneth et al. | |
| 2006/0111614 A1 | 5/2006 | Saadat et al. | |
| 2006/0122587 A1 | 6/2006 | Sharareh | |
| 2006/0146172 A1 | 7/2006 | Jacobsen et al. | |
| 2006/0149129 A1 | 7/2006 | Watts et al. | |

(56) References Cited

U.S. PATENT DOCUMENTS

| | | |
|---|---|---|
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima et al. |
| 2006/0184048 A1* | 8/2006 | Saadat ............ A61B 1/0008 600/478 |
| 2006/0195060 A1* | 8/2006 | Navia ............... A61F 2/90 604/96.01 |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1* | 11/2006 | Chin ............... A61B 18/1482 606/41 |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083099 A1 | 4/2007 | Henderson et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0239010 A1 | 10/2007 | Johnson |
| 2007/0265609 A1 | 11/2007 | Thapliyal et al. |
| 2007/0265610 A1 | 11/2007 | Thapliyal et al. |
| 2007/0270639 A1 | 11/2007 | Long |
| 2007/0270686 A1 | 11/2007 | Ritter et al. |
| 2007/0282371 A1 | 12/2007 | Lee et al. |
| 2007/0287886 A1* | 12/2007 | Saadat ............ A61B 1/0008 600/115 |
| 2007/0293724 A1* | 12/2007 | Saadat ............ A61B 1/0008 600/156 |
| 2008/0009747 A1 | 1/2008 | Saadat et al. |
| 2008/0009859 A1 | 1/2008 | Auth et al. |
| 2008/0015445 A1* | 1/2008 | Saadat ............ A61B 1/0008 600/470 |
| 2008/0015563 A1 | 1/2008 | Hoey et al. |
| 2008/0015569 A1 | 1/2008 | Saadat et al. |
| 2008/0027464 A1* | 1/2008 | Moll ............... A61B 1/307 606/130 |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058650 A1* | 3/2008 | Saadat ............ A61M 25/1002 600/478 |
| 2008/0058836 A1 | 3/2008 | Moll et al. |
| 2008/0097476 A1* | 4/2008 | Peh ............... A61B 1/0008 606/130 |
| 2008/0183081 A1 | 7/2008 | Lys et al. |
| 2008/0214889 A1 | 9/2008 | Saadat et al. |
| 2008/0228032 A1 | 9/2008 | Starksen et al. |
| 2008/0234834 A1* | 9/2008 | Meade ............ A61B 17/221 623/23.65 |
| 2008/0275300 A1 | 11/2008 | Rothe et al. |
| 2008/0287790 A1 | 11/2008 | Li |
| 2008/0287805 A1 | 11/2008 | Li |
| 2008/0319258 A1* | 12/2008 | Thompson ........ A61B 1/00135 600/104 |
| 2009/0030276 A1 | 1/2009 | Saadat et al. |
| 2009/0030412 A1 | 1/2009 | Willis et al. |
| 2009/0048480 A1 | 2/2009 | Klenk et al. |
| 2009/0054805 A1* | 2/2009 | Boyle, Jr. ........ A61B 10/0266 600/564 |
| 2009/0062790 A1* | 3/2009 | Malchano ........ A61B 18/1492 606/41 |
| 2009/0062871 A1* | 3/2009 | Chin ............... A61B 1/00082 606/86 R |
| 2009/0076489 A1 | 3/2009 | Welches et al. |
| 2009/0076498 A1* | 3/2009 | Saadat ............ A61B 18/1492 606/41 |
| 2009/0082623 A1 | 3/2009 | Rothe et al. |
| 2009/0125022 A1 | 5/2009 | Saadat et al. |
| 2009/0143640 A1* | 6/2009 | Saadat ............ A61B 1/00089 600/104 |
| 2009/0187074 A1 | 7/2009 | Saadat et al. |
| 2009/0203962 A1 | 8/2009 | Miller et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0130836 A1 | 5/2010 | Malchano et al. |
| 2011/0060227 A1* | 3/2011 | Saadat ............ A61B 1/0008 600/476 |
| 2011/0060298 A1 | 3/2011 | Saadat |
| 2011/0144576 A1 | 6/2011 | Rothe et al. |
| 2011/0196237 A1 | 8/2011 | Pelissier et al. |
| 2012/0016221 A1 | 1/2012 | Saadat et al. |
| 2012/0059366 A1 | 3/2012 | Drews et al. |
| 2012/0095332 A1 | 4/2012 | Nitta et al. |
| 2012/0150046 A1 | 6/2012 | Watson et al. |
| 2013/0172745 A1 | 7/2013 | Choi |
| 2014/0012074 A1 | 1/2014 | Vazales et al. |
| 2015/0094577 A1 | 4/2015 | Saadat et al. |
| 2015/0094582 A1 | 4/2015 | Tanaka et al. |
| 2015/0190036 A1 | 7/2015 | Saadat |
| 2015/0250382 A1 | 9/2015 | Saadat et al. |
| 2016/0038005 A1 | 2/2016 | Saadat et al. |
| 2016/0095501 A1 | 4/2016 | Saadat et al. |
| 2016/0227989 A1 | 8/2016 | Saadat et al. |
| 2016/0361040 A1 | 12/2016 | Tanaka et al. |
| 2017/0071460 A1 | 3/2017 | Miller et al. |
| 2018/0228350 A1 | 8/2018 | Saadat et al. |
| 2019/0008360 A1 | 1/2019 | Peh et al. |
| 2019/0014975 A1 | 1/2019 | Saadat et al. |
| 2019/0021577 A1 | 1/2019 | Peh et al. |
| 2019/0046013 A1 | 2/2019 | Saadat et al. |
| 2019/0125166 A1 | 5/2019 | Saadat |
| 2019/0307331 A1 | 10/2019 | Saadat et al. |
| 2019/0343373 A1 | 11/2019 | Saadat et al. |
| 2020/0000319 A1 | 1/2020 | Saadat |

FOREIGN PATENT DOCUMENTS

| | | |
|---|---|---|
| EP | 0283661 A2 | 9/1988 |
| EP | 0301288 A1 | 2/1989 |
| EP | 0842673 A1 | 5/1998 |
| JP | S5993413 A | 5/1984 |
| JP | S59181315 A | 10/1984 |
| JP | H01221133 A | 9/1989 |
| JP | H03284265 A | 12/1991 |
| JP | H05103746 A | 4/1993 |
| JP | H06507809 A | 9/1994 |
| JP | H0951897 A | 2/1997 |
| JP | H11299725 A | 11/1999 |
| JP | 2001504363 A | 4/2001 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9740880 A1 | 11/1997 |
| WO | WO-9818388 A1 | 5/1998 |
| WO | WO-0024310 A1 | 5/2000 |
| WO | WO-0149356 A1 | 7/2001 |
| WO | WO-0172368 A2 | 10/2001 |
| WO | WO-0230310 A1 | 4/2002 |
| WO | WO-03037416 A1 | 5/2003 |
| WO | WO-03039350 A2 | 5/2003 |
| WO | WO-03053491 A2 | 7/2003 |

(56) References Cited

FOREIGN PATENT DOCUMENTS

| | | |
|---|---|---|
| WO | WO-03073942 A2 | 9/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |
| WO | WO-2006091597 A1 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Avitall, et al. "A Catheter System to Ablate Atrial Fibrillation in a Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.

Bhakta D., et al., "Principles of Electroanatomic Mapping," Indian Pacing and Electrophysiology Journal, 2008, vol. 8 (1), pp. 32-50.

Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010]. Retrieved from the Internet< URL: http://www.ncbi.nlm.nih.gov/sites/entrez>.

Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.

Communication from the Examining Division for Application No. EP06734083.6 dated Nov. 12, 2010, 3 pages.

Communication from the Examining Division for Application No. EP06734083.6 dated Oct. 23, 2009, 1 page.

Communication from the Examining Division of Application No. EP08746822.9 dated Jul. 13, 2010, 1 page.

Co-pending U.S. Appl. No. 61/286,283, filed Dec. 14, 2009.

Co-pending U.S. Appl. No. 61/297,462, filed Jan. 22, 2010.

Cox J.L., "Cardiac Surgery for Arrhythmias," Journal of Cardiovascular Electrophysiology, 2004, vol. 15, pp. 250-262.

Cox J.L., et al., "Five-Year Experience With the Maze Procedure for Atrial Fibrillation," The Annals of Thoracic Surgery, 1993, vol. 56, pp. 814-824.

Cox J.L., et al., "Modification of the Maze Procedure for Atrial Flutter and Atrial Fibrillation," The Journal of Thoracic and Cardiovascular Surgery, 1995, vol. 110, pp. 473-484.

Cox J.L., "The Status of Surgery for Cardiac Arrhythmias," Circulation, 1985, vol. 71, pp. 413-417.

Cox J.L., "The Surgical Treatment of Atrial Fibrillation," The Journal of Thoracic and Cardiovascular Surgery, 1991, vol. 101, pp. 584-592.

Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet:< URL: http://circ.ahajournals.org/cgi/content/full/91/8/2235>.

Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.

Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.

European Search Report for Application No. EP07799466.3 dated Nov. 18, 2010, 9 pages.

European Search Report for Application No. EP08746822.9 dated Mar. 29, 2010, 7 Pages.

Examination Communication for Application No. EP06734083.6 dated May 18, 2010, 3 Pages.

Extended European Search Report for Application No. EP06734083.6 dated Jul. 1, 2009, 6 pages.

Extended European search report for Application No. EP20070758716 dated Feb. 28, 2011, 8 Pages.

Extended European search report for Application No. EP20070799466 dated Nov. 18, 2010, 9 Pages.

Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.

Final Office Action dated Mar. 1, 2010 for U.S. Appl. No. 12/117,655, filed May 8, 2008.

Final Office Action dated Jun. 2, 2011 for U.S. Appl. No. 12/117,655, filed May 8, 2008.

Final Office Action dated Oct. 5, 2010 for U.S. Appl. No. 11/810,850, filed Jun. 7, 2007.

Final Office Action dated May 12, 2011 for U.S. Appl. No. 11/775,771, filed Jul. 10, 2007.

Final Office Action dated Sep. 16, 2010 for U.S. Appl. No. 11/828,267, filed Jul. 25, 2007.

Hoey M.F., et al., "Intramural Ablation Using Radiofrequency Energy via Screw-Tip Catheter and Saline Electrode," Pacing and Clinical Electrophysiology, 1995, vol. 18, Part II, 487.

Huang, "Increase in the Lesion Size and Decrease in the Impedance Rise with a Saline Infusion Electrode Catheter for Radiofrequency," Circulation, 1989, vol. 80 (4), II-324.

International Search Report and Written Opinion for Application No. PCT/US2007/073184, dated Aug. 12, 2012, 7 pages.

International Search Report for Application No. PCT/US2006/003288, dated Aug. 9, 2007, 1 page.

International Search Report for Application No. PCT/US2007/064195, dated Dec. 7, 2007, 1 page.

International Search Report for Application No. PCT/US2007/071226, dated Sep. 4, 2008, 1 page.

International Search Report for Application No. PCT/US2007/077429, dated Apr. 7, 2008, 1 page.

Moser K.M ., et al., "Angioscopic Visualization of Pulmonary Emboli," Chest, 1980, vol. 77 (2), pp. 198-201.

Nakamura F., et al., "Percutaneous Intracardiac Surgery With Cardioscopic Guidance," SPIE, 1992, vol. 1642, pp. 214-216.

Non-Final Office Action dated Jun. 7, 2011 for U.S. Appl. No. 12/323,281, filed Nov. 25, 2008.

Non-Final Office Action dated Aug. 8, 2011 for U.S. Appl. No. 12/464,800, filed May 12, 2009.

Non-Final Office Action dated Jun. 8, 2009 for U.S. Appl. No. 12/117,655, filed May 8, 2008.

Non-Final Office Action dated May 9, 2011 for U.S. Appl. No. 11/961,950, filed Dec. 20, 2007.

Non-Final Office Action dated May 9, 2011 for U.S. Appl. No. 11/961,995, filed Dec. 20, 2007.

Non-Final Office Action dated May 9, 2011 for U.S. Appl. No. 11/962,029, filed Dec. 20, 2007.

Non-Final Office Action dated Jun. 10, 2010 for U.S. Appl. No. 11/560,742, filed Nov. 16, 2006.

Non-Final Office Action dated Apr. 11, 2011 for U.S. Appl. No. 11/763,399, filed Jun. 14, 2007.

(56) References Cited

OTHER PUBLICATIONS

Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.
Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Mar. 16, 2010 for U.S. Appl. No. 11/810,850, filed Jun. 7, 2007.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated May 20, 2011 for U.S. Appl. No. 11/877,386, filed Oct. 23, 2007.
Non-Final Office Action dated Jul. 21, 2010 for U.S. Appl. No. 11/687,597, filed Mar. 16, 2007.
Non-Final Office Action dated Apr. 22, 2011 for U.S. Appl. No. 12/367,019, filed Feb. 6, 2009.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,158, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Aug. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Jun. 13, 2011 for Japanese Application No. 2007-554156 filed Jan. 30, 2006.
Notice of Allowance dated Nov. 15, 2010 for U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.
Notice of Allowance dated Feb. 24, 2011 for U.S. Appl. No. 11/687,597, filed Mar. 16, 2007.
Office Action dated Feb. 15, 2011 for Japanese Application No. 2007-554156 filed Jan. 30, 2006.
Office Action dated Apr. 27, 2011 for Japanese Application No. 2009-500630 filed Mar. 16, 2007.
Pappone C., et al., "Circumferential Radiofrequency Ablation of Pulmonary Vein Ostia," Circulation, 2000, vol. 102, pp. 2619-2628.
Sethi K.K., et al., "Transseptal catheterization for the electrophysiologist: modification with a 'view'," Journal of Interventional Cardiac Electrophysiology, 2001, vol. 5 (1), pp. 97-99.
Tse HF., et al., "Angiogenesis in Ischaemic Myocardium by Intramyocardial Autologous Bone Marrow Mononuclear Cell Implantation," Lancet, 2003, vol. 361, pp. 47-49.
Supplemental European Search Report for Application No. EP07758716 dated Feb. 28, 2011, 8 Pages.
Supplementary European search report for Application No. EP07812146.4 dated Nov. 18, 2010, 8 Pages.
Supplementary European Search Report for Application No. EP07841754, dated Jun. 30, 2010, 6 pages.
Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.
Uchida Y., "Developmental History of Cardioscopes", in: Coronary Angioscopy, Chapter 19, Futura Publishing Company, Inc., 2001, pp. 187-197.
Willkampf F.H., et al., "Radiofrequency Ablation with a Cooled Porous Electrode Catheter," JACC, Abstract,1988, vol. 11 (2), pp. 17A.
Written Opinion for Application No. PCT/US2006/003288, dated Aug. 9, 2007, 6 pages.
Written Opinion for Application No. PCT/US2007/064195, dated Dec. 7, 2007, 5 pages.
Written Opinion for Application No. PCT/US2007/071226, dated Sep. 4, 2008, 4 page.
Written Opinion for Application No. PCT/US2007/077429, dated Apr. 7, 2008, 5 pages.

* cited by examiner

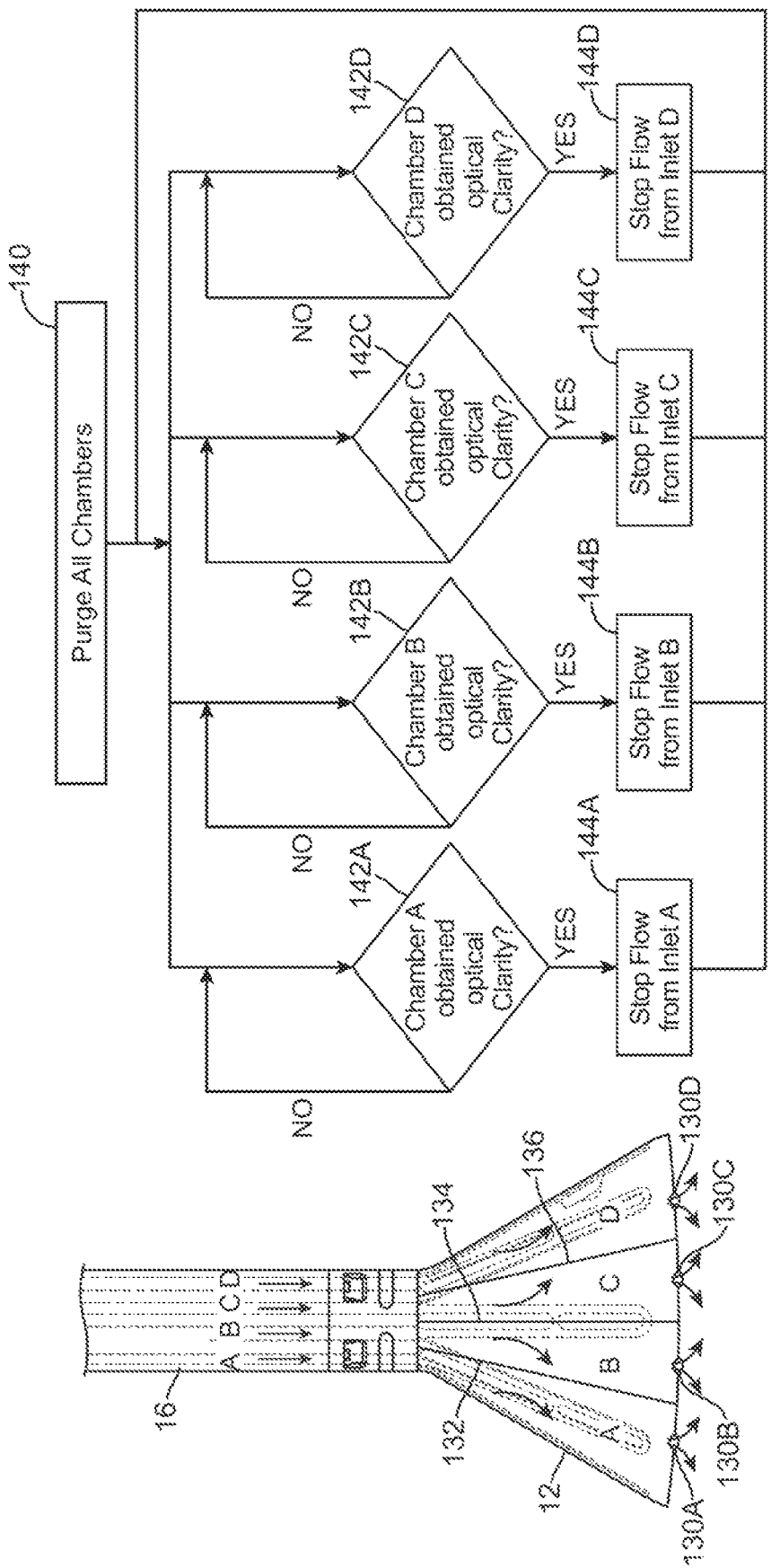

METHODS AND APPARATUS FOR EFFICIENT PURGING

CROSS-REFERENCE TO RELATED APPLICATIONS

This application is a division of U.S. patent application Ser. No. 15/350,796, filed Nov. 14, 2016 which is a Continuation of U.S. patent application Ser. No. 12/499,681, filed Jul. 8, 2009 which claims the benefit of priority to U.S. Prov. Pat. App. 61/079,414, filed Jul. 9, 2008, all of which are incorporated herein by reference in their entirety. U.S. patent application Ser. No. 12/499,681 is also a continuation-in-part of U.S. patent application Ser. No. 11/259,498, filed Oct. 25, 2005 (now U.S. Pat. No. 7,860,555), which claims the benefit of priority to U.S. Prov. Pat. App. No. 60/649,246 filed Feb. 2, 2005, all of which are incorporated by reference herein in their entirety.

FIELD OF THE INVENTION

The present invention relates generally to medical devices used for accessing, visualizing, and/or treating regions of tissue within a body. More particularly, the present invention relates to methods and apparatus for efficiently purging opaque fluids from an intravascular visualization system to facilitate visualization and/or treatment of the tissue.

BACKGROUND OF THE INVENTION

Conventional devices for accessing and visualizing interior regions of a body lumen are known. For example, various catheter devices are typically advanced within a patient's body, e.g., intravascularly, and advanced into a desirable position within the body. Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, many of the conventional catheter imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Conventional catheter techniques and devices, for example such as those described in U.S. Pat. Nos. 5,895,417; 5,941,845; and 6,129,724, used on the epicardial surface of the heart may be difficult in assuring a transmural lesion or complete blockage of electrical signals. In addition, current devices may have difficulty dealing with varying thickness of tissue through which a transmural lesion is desired.

Conventional accompanying imaging devices, such as fluoroscopy, are unable to detect perpendicular electrode orientation, catheter movement during the cardiac cycle, and image catheter position throughout lesion formation. The absence of real-time visualization also poses the risk of incorrect placement and ablation of structures such as sinus node tissue which can lead to fatal consequences.

BRIEF SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

One variation of an imaging hood may incorporate an internal diaphragm, which may be transparent, attached to the inner wall of the hood about its circumference. The diaphragm may be fabricated from a transparent elastomeric membrane similar to the material of the hood (such as polyurethane, Chronoflex™, latex, etc) and may define one or more apertures through which saline fluid introduced into the hood may pass through the diaphragm and out through the main aperture to clear blood from the open field within the hood. The one or more apertures may have a diameter of between, e.g., 1 mm to 0.25 mm.

Flow of the saline fluid out of the hood through the main aperture may continue under relatively low fluid pressure conditions as saline is introduced from the catheter shaft, through the diaphragm apertures, and out of the main aperture. Upon the application of a relatively higher fluid pressure, the diaphragm may be pushed distally within the hood until it extends or bulges distally to block the main aperture until fluid flow out of the hood is reduced or completely stopped. With the aperture blocked, the hood may retain the purging fluid within to facilitate visualization through the fluid of the underlying tissue. Thus, the hood may be panned around a target tissue region with sustained visualization to reduce the amount of saline that is introduced into a patient's heart or bloodstream. Once the fluid pressure of the purging fluid is reduced, the diaphragm may retract to unblock the aperture and thus allow for the flow of the purging fluid again through the diaphragm apertures and main aperture. Alternatively, one or more unidirectional valves may be positioned over the diaphragm to control the flow of the purging fluid through the hood and out the main aperture. Other variations may incorporate an internal inflation member or pouch which may be positioned within the hood and which controls the outflow of the purged saline based on the fluid pressure within the pouch.

In yet other variations, one or more portions of the hood support struts may extend at least partially within the distal chamber such that the saline within the distal chamber can be electrically charged, such as with RF energy, when the support struts are coupled to an RF generator. This allows the saline encapsulated in the distal chamber to function as a virtual electrode by conducting the discharged energy to the underlying visualized tissue for treatments, such as tissue ablation.

Yet another variation may incorporate an electrode, such as ring-shaped electrode, within the hood which defines a central lumen therethrough. The central lumen may define one or more fluid apertures proximally of the electrode which open to the hood interior in a circumferential pattern around an outer surface of the lumen. With the positioning of, e.g., a fiberscope, within the lumen and its distal end positioned adjacent to or distal to the electrode, the distal opening of the lumen may be obstructed by the fiberscope such that the purging fluid introduced through the lumen flows in an annular space between the fiberscope and the lumen and is forced to flow sideways into the hood through the one or more fluid apertures while the distal opening of the lumen remains obstructed by the fiberscope.

Another variation of the hood may incorporate one or more protrusions or projections extending from a distal membrane over the hood. These protrusions or projections may extend distally adjacent to a corresponding unidirectional valve which has overlapping leaflets. As the hood is filled with the purging fluid, flow through the valves is inhibited or prevented by the overlapping leaflets but as the distal face of the hood membrane is pressed against a surface of tissue to be visualized and/or treated, the protrusions or projections pressing against the tissue surface may force the valve leaflets to separate temporarily, thus allowing the passage of saline out through the valves to clear any blood within the hood as well as any blood between membrane and the tissue surface.

In yet another variation, an imaging hood may be configured to form a recirculating flow inside the hood. The purging fluid may be introduced (e.g., injected) as well as withdrawn from the imaging hood interior through two different lumens in the catheter shaft. For instance, the fluid may be introduced by an inlet lumen which injects the fluid along a first path into the hood while the recirculating fluid may be withdrawn by suction through a separate outlet lumen. By keeping a relatively higher volume flow rate in the inlet lumen for injecting the purging fluid than the flow rate in the outlet lumen for withdrawing it, a considerable amount of purging fluid may be conserved resulting in efficient hood purging. Another variation may incorporate a suction lumen, e.g., a pre-bent lumen, extending from the catheter directly to the main aperture. This particular variation may allow for the direct evacuation of blood through a lumen opening at a particular location along the main aperture where the in-flow of blood (or other opaque fluids) is particularly high.

Yet another variation may utilize a hood partitioned into multiple chambers which are in fluid communication with individual corresponding fluid lumens defined through the catheter. Each of the chambers may be separated by corresponding transparent barriers which extend along the length of hood. Each of the different chambers may have a corresponding aperture. Efficient purging and reduction of saline discharged may achieved when purging can be selectively stopped once a particular chamber establishes optical clarity. This can be done manually by the operator or through automation by a processor incorporated within the system.

Another variation may incorporate an expandable distal membrane which projects distally from the hood and is sufficiently soft to conform against the underlying contacted tissue. With the membrane defining one or more hood apertures, the purging fluid may enter within the hood and exit through the hood apertures into an intermediate chamber. The purging fluid may exit the intermediate chamber through at least one central aperture. In the event that the hood contacts against a surface of tissue at a non-perpendicular angle, the distal membrane may still conform to the tissue surface.

In yet another variation, an imaging hood may have a distal membrane without an aperture and which may be filled with the purging fluid once desirably positioned within the subject's body in proximity to the tissue region to be visualized and/or treated. Once a tissue region to be treated has been located by the hood, a piercing instrument may be advanced through the hood from the catheter to puncture through the distal membrane at a desired site. This may form a puncture aperture through which the purging fluid may escape. Hence, purging is only performed at locations where instruments are passed out of the imaging hood thus reducing the amount of saline discharged out of the hood.

BRIEF DESCRIPTION OF THE DRAWINGS

FIG. 15 shows a side view of another variation which comprises multiple chambers each defining an aperture to form a uniform flow through the hood.

FIG. 16 illustrates a flow chart of one example for automating the selective purging of individual chambers to reduce saline discharge from the hood.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
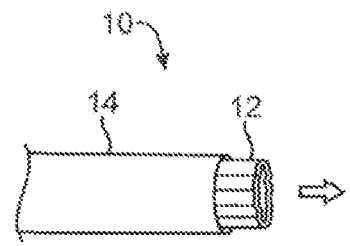
FIG. 1A shows a side view of one variation of a tissue imaging apparatus during deployment from a sheath or delivery catheter.
Figure 1B:
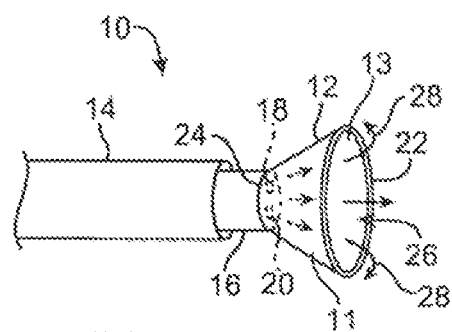
FIG. 1B shows the deployed tissue imaging apparatus of FIG. 1A having an optionally expandable hood or sheath attached to an imaging and/or diagnostic catheter.
Figure 1C:
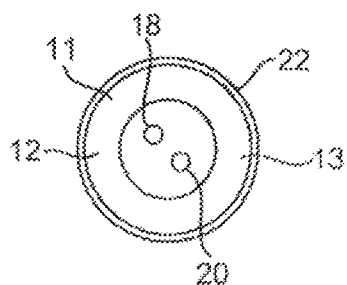
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
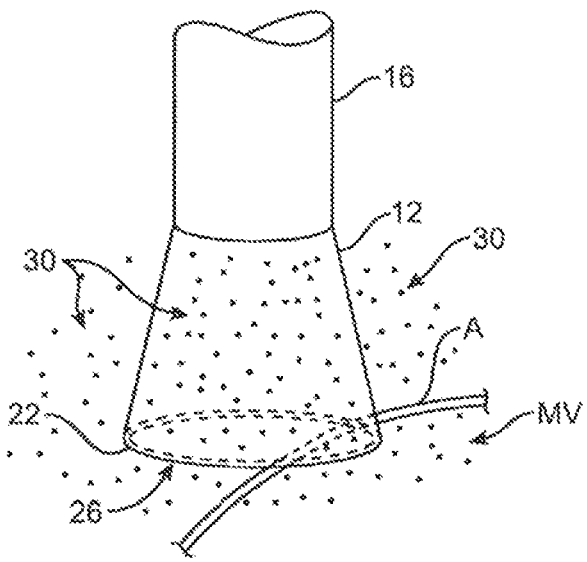
FIGS. 2A and 2B show one example of a deployed tissue imager positioned against or adjacent to the tissue to be imaged and a flow of fluid, such as saline, displacing blood from within the expandable hood.
Figure 2B:
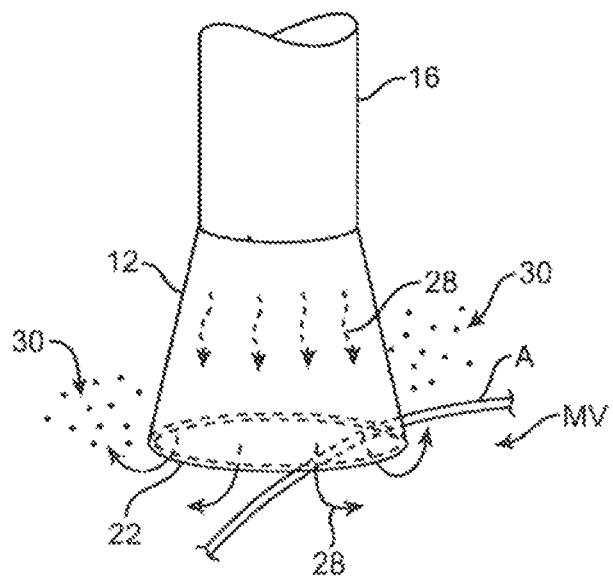

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
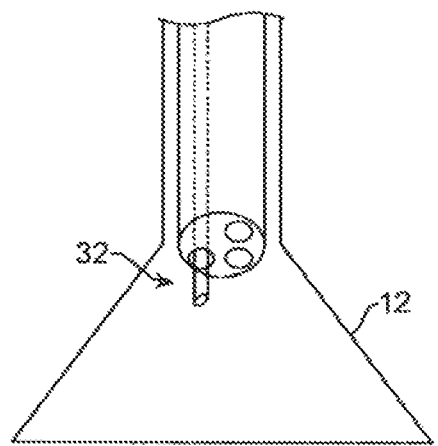
FIGS. 3A and 3B show examples of various visualization imagers which may be utilized within or along the imaging hood.
Figure 3B:
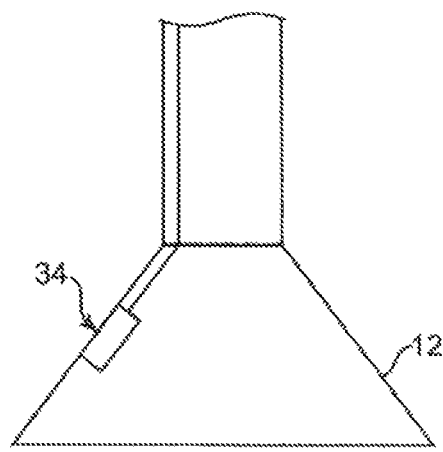

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
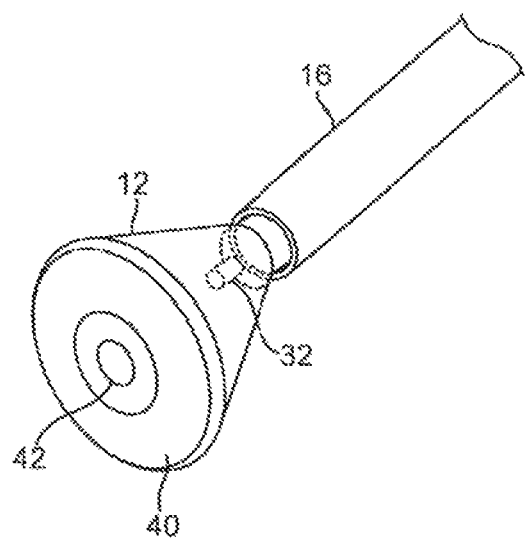
FIGS. 4A and 4B show perspective and end views, respectively, of an imaging hood having at least one layer of a transparent elastomeric membrane over the distal opening of the hood.
Figure 4B:
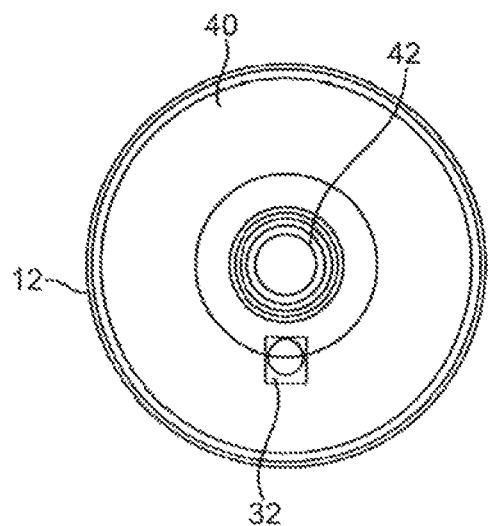

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
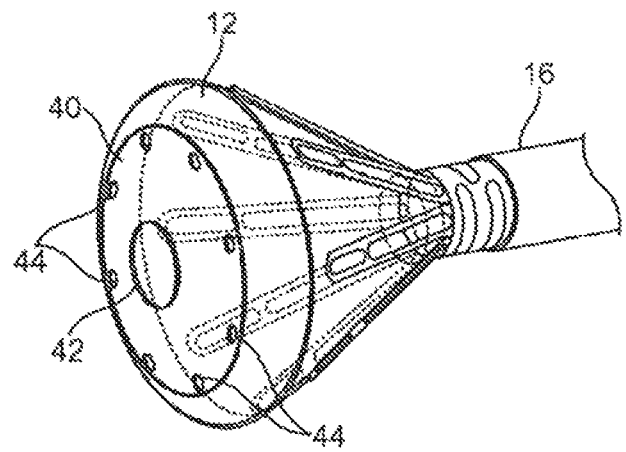
FIGS. 5A and 5B show perspective and end views, respectively, of an imaging hood which includes a membrane with an aperture defined therethrough and a plurality of additional openings defined over the membrane surrounding the aperture.
Figure 5B:
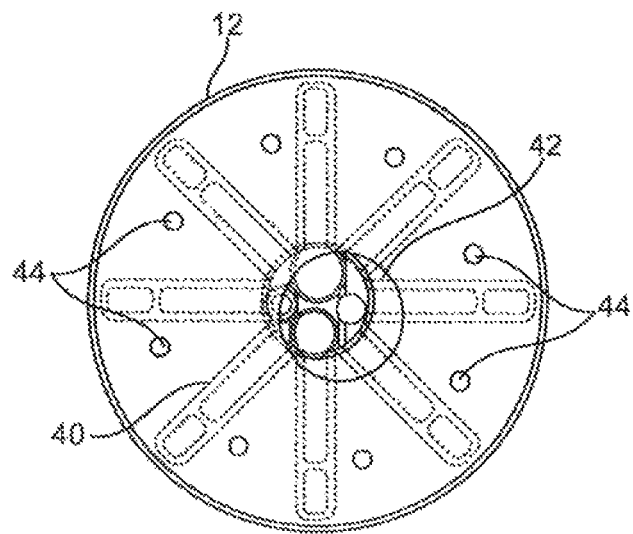

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Figure 6A:
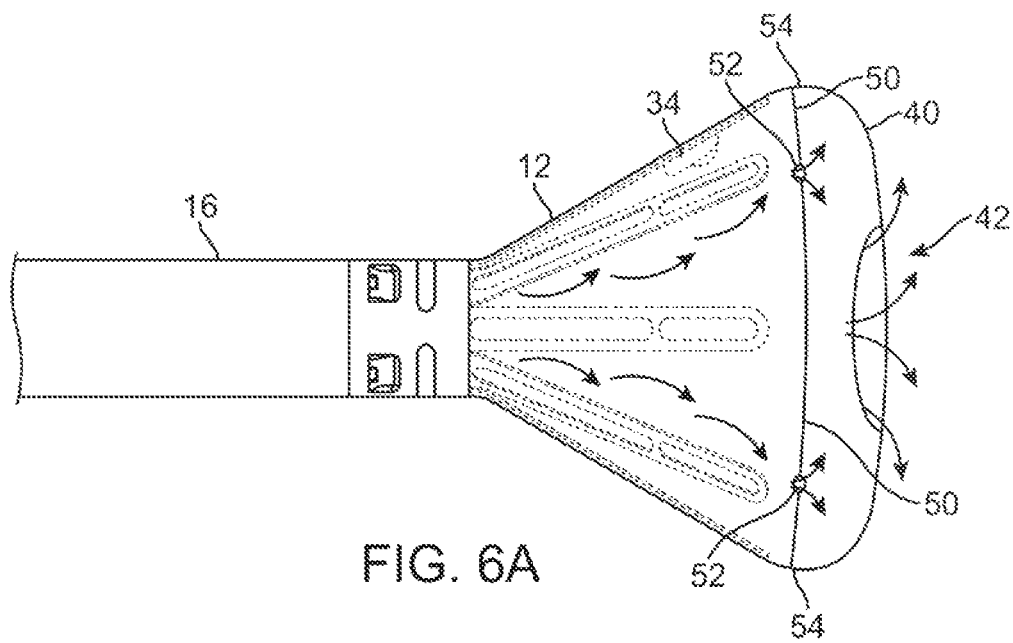
FIGS. 6A and 6B show side views of one variation of the imaging hood having an internal diaphragm in which the flow of the purging fluid through the hood can be controlled or stopped by varying its fluid pressure.
Figure 6B:
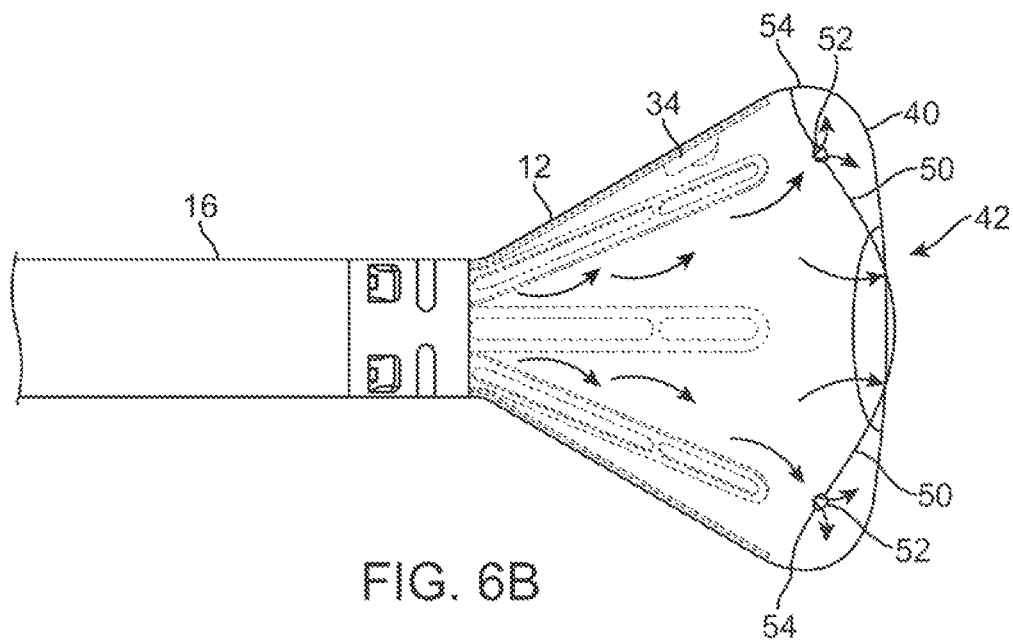

FIGS. 6A and 6B show side views of one variation of an imaging hood incorporating an internal diaphragm 50, which may be transparent, attached to the inner wall of the hood 12 about its circumference 54 such that diaphragm 50 is suspended circumferentially within the hood 12. The diaphragm 50 may be fabricated from a transparent elastomeric membrane similar to the material of hood 12 (such as polyurethane, Chronoflex™, latex, etc) and may define one or more apertures 52 through which saline fluid introduced into hood 12 may pass through diaphragm 50 and out through main aperture 42 to clear blood from the open field within hood 12. The one or more apertures 52 may have a diameter of between, e.g., 1 mm to 0.25 mm.

Flow of the saline fluid out of the hood 12 through main aperture 42 may continue under relatively low fluid pressure conditions as saline is introduced from the catheter shaft 16, through the diaphragm apertures 52, and out of the main aperture 42, as shown in FIG. 6A. Upon the application of a relatively higher fluid pressure, the diaphragm 50 may be pushed distally within hood 12 until it extends or bulges distally to block the main aperture 42 until fluid flow out of the hood 12 is reduced or completely stopped, as shown in FIG. 6B. With aperture 42 blocked, the hood 12 may retain the purging fluid within to facilitate visualization through the fluid of the underlying tissue. Thus, hood 12 may be panned around a target tissue region with sustained visualization to reduce the amount of saline that is introduced into a patient's heart or bloodstream. Once the fluid pressure of the purging fluid is reduced, diaphragm 50 may retract to unblock aperture 42 and thus allow for the flow of the purging fluid again through diaphragm apertures 52 and main aperture 42.

Figure 7A:
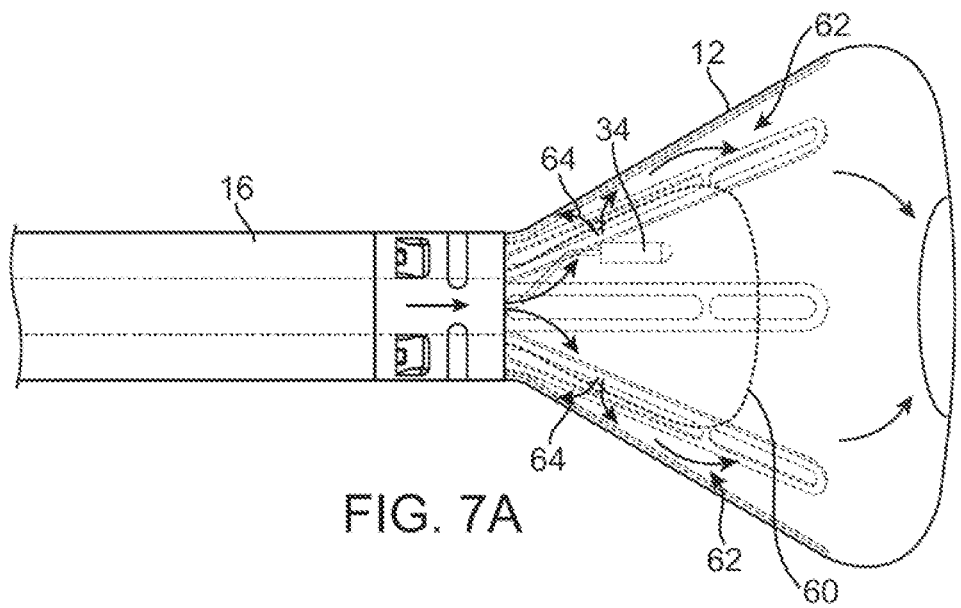
FIGS. 7A and 7B show side views of another variation of the hood having an inflatable membrane positioned within the hood which may be used to control or stop the purging fluid.
Figure 7B:
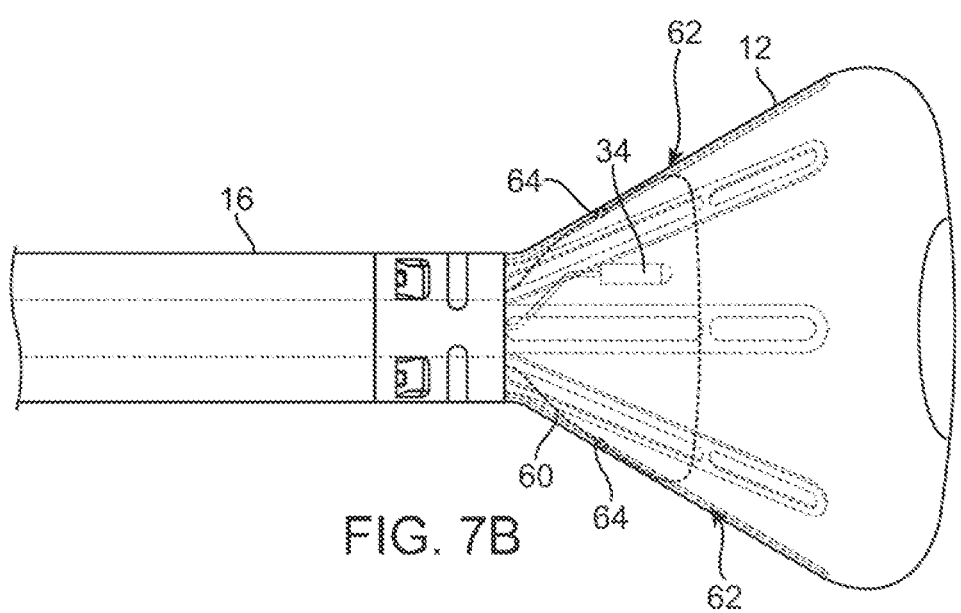

Another variation is shown in the side views of FIGS. 7A and 7B, which show an internal inflation member or pouch 60, which may be transparent, positioned within hood 12 which also controls the outflow of the purged saline based on fluid pressure. When internal inflation member of pouch 60 is at least partially inflated via the purging fluid introduced within, an annular flow path 62 may be defined between an external surface of pouch 60 and an inner surface of hood 12, as illustrated in FIG. 7A. The purging fluid may be initially introduced into pouch 60 and then flow through one or more apertures 64 defined along the surface of pouch 60 and out through the main aperture of hood 12 to clear blood therefrom. Each of the one or more apertures 64 may have a diameter ranging from, e.g., 1 mm to 0.25 mm, and the apertures 64 may be located along a proximal side of the pouch 60 along the annular flow path 62 in apposition to an interior surface of hood 12. When the pressure of the purging fluid is increased, the internal pouch 60 may expand into contact against the inner surface of hood 12 to block flow path 62 and pouch apertures 64 against hood 12, as depicted in FIG. 7B, thereby reducing or stopping saline outflow from the imaging hood 12. As the fluid pressure of the purging fluid is reduced, the size of internal pouch 60 may retract to thus unblock apertures 64 and flow path 62 and again allow for the flow of the fluid therethrough.

Figure 8:
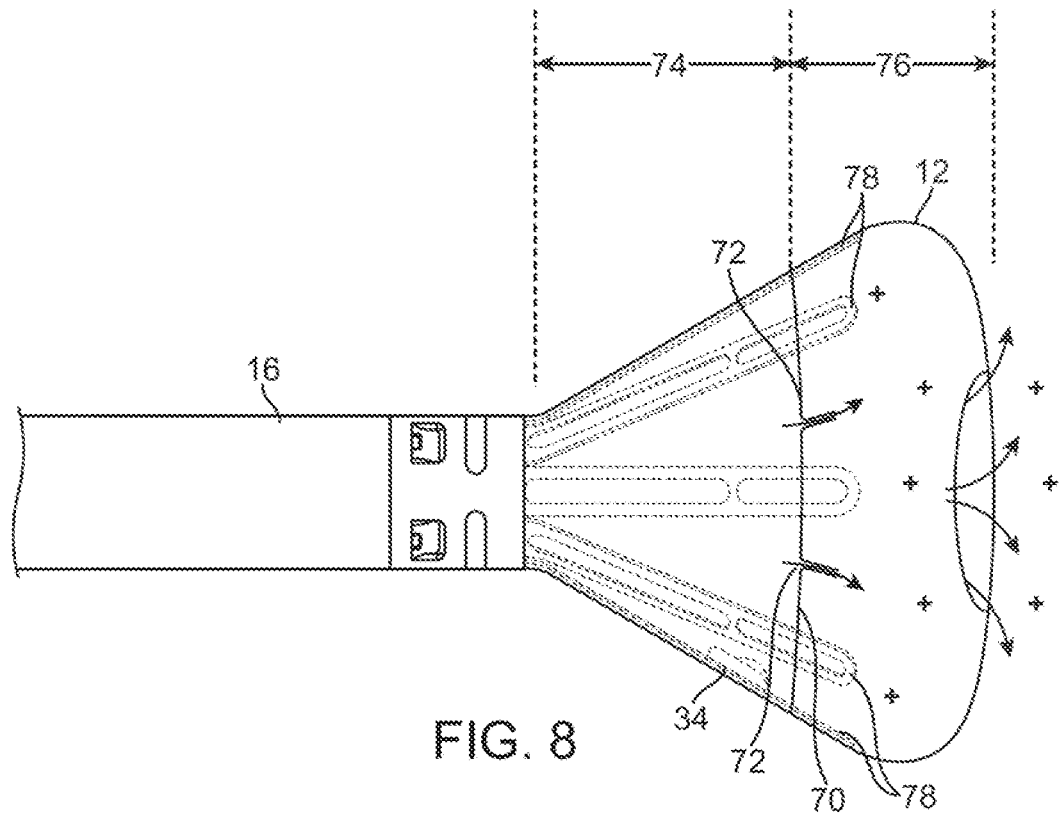
FIG. 8 shows a side view of another variation having an internal membrane which comprises one or more unidirectional valves to control the flow of the purging fluid.
Figure 9A:
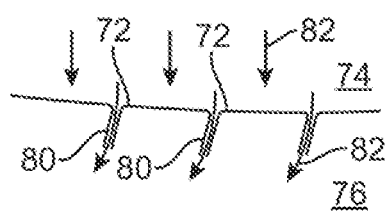
FIGS. 9A and 9B show side views of the one or more unidirectional valves in an opened and closed configuration, respectively, for controlling the fluid flow therethrough.
Figure 9B:
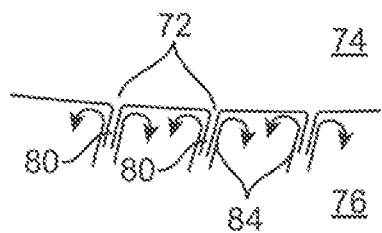

In yet another variation shown in the side view of FIG. 8, hood 12 may be sectioned into a proximal chamber 74 and a distal chamber 76 separated by a transparent diaphragm 70 suspended within the hood 12, as previously described. In this embodiment, one or more unidirectional valves 72 may be positioned over the diaphragm 70 through which the purging fluid may flow from the proximal chamber 74 to the distal chamber 76 and through the main aperture. Because of the unidirectional flow of the fluid through valves 72, the purging fluid may exit proximal chamber 74 but may not flow back through the valves 72. In this manner, while the main aperture on the base of the hood 12 may temporarily allow the entry of blood back into the distal chamber 76, the blood is prevented from filling the entire hood 12 by the valves 72 and the proximal chamber 74 may be purged once to initially clear away blood to obtain optical clarity. Hence the volume required for constant clearing of opaque fluids, such as blood, is reduced thus reducing the amount of saline required to establish visualization. FIGS. 9A and 9B show detail cross-sectional side views of the one or more unidirectional valves 72. As shown in FIG. 9A, flow 82 from the proximal chamber 74 may open overlapping valve leaflets 80, which extend distally into distal chamber 76. Once the flow 82 is stopped or reduced, the backflow 84 from distal chamber 76 may collapse the valve leaflets 80 upon themselves, thus inhibiting backflow through the valves 72 and into proximal chamber 74, as shown in FIG. 9B.

As further shown in FIG. 8, one or more portions 78 of the hood support struts which extend at least partially within the distal chamber 76 may be internally exposed such that the saline within the distal chamber 76 can be electrically charged, such as with RF energy, when the support struts are coupled to an RF generator. This allows the saline encapsulated in the distal chamber 76 to function as a virtual electrode by conducting the discharged energy to the underlying visualized tissue for treatments, such as tissue ablation. Details of electrode ablation of visualized tissue which may be utilized with apparatus and methods described herein are described in further detail in U.S. patent application Ser. No. 12/118,439 filed May 9, 2008 (U.S. Pat. Pub. 2009/0030412 A1), which is incorporated herein by reference in its entirety.

Figure 10A:
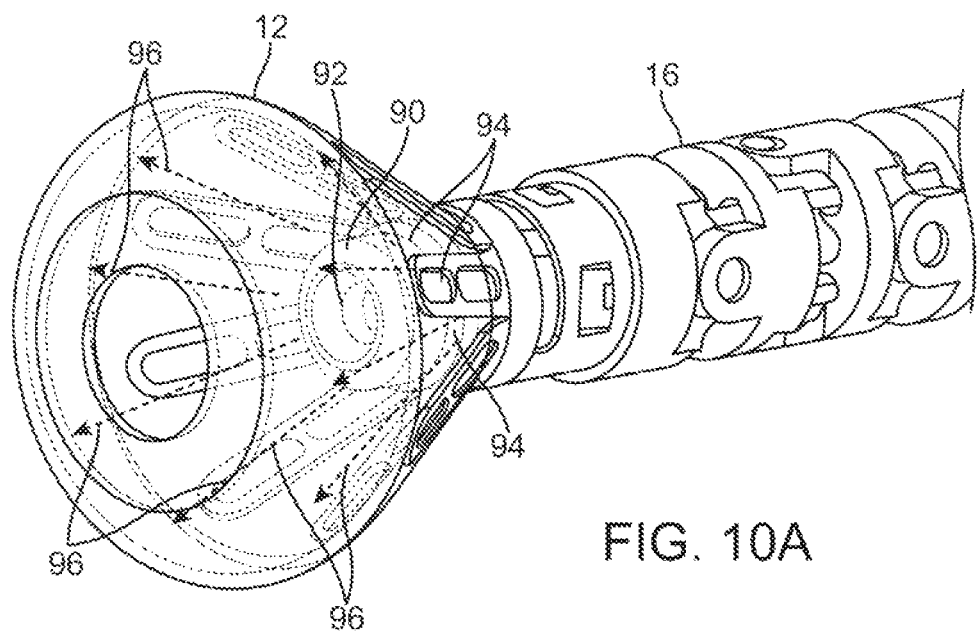
FIGS. 10A and 10B show perspective and cross-sectional perspective views, respectively, of yet another variation where one or more side ports may be defined within the hood for uniformly purging blood from the hood interior.
Figure 10B:
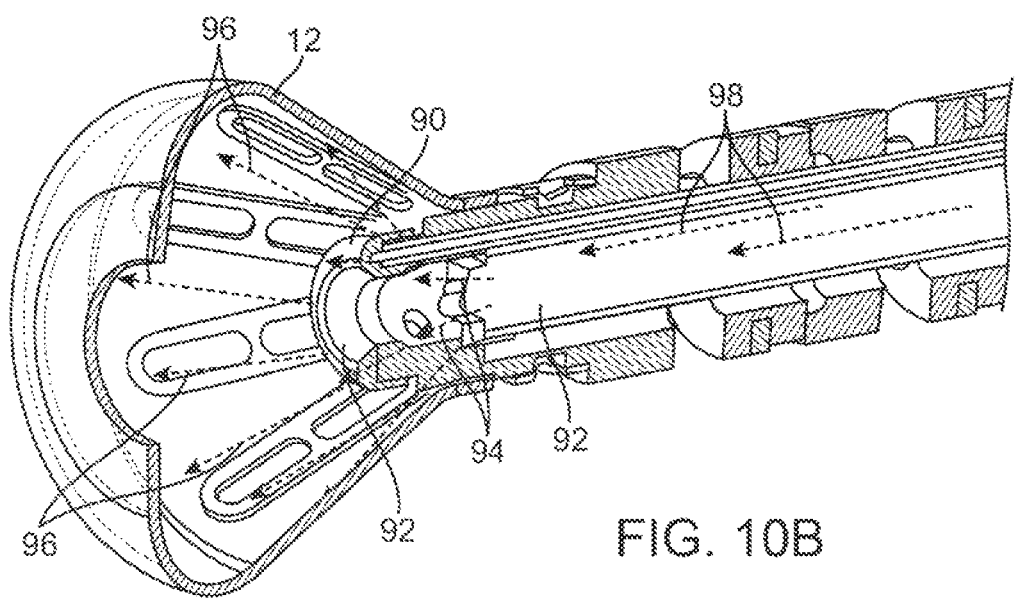

FIGS. 10A and 10B show perspective and cross-sectional perspective views of yet another variation which incorporates an electrode 90, such as ring-shaped electrode, within hood 12 which defines a central lumen 92 therethrough. The central lumen 92 may define one or more fluid apertures 94 proximally of electrode 90 which open to the hood interior in a circumferential pattern around an outer surface of lumen 92. Central lumen 92 may also be sized to allow for the introduction and advancement of a fiberscope (or other instrument) therethrough. With the positioning of, e.g., a fiberscope, within lumen 92 and its distal end positioned adjacent to or distal to electrode 90, the distal opening of lumen 92 may be obstructed by the fiberscope. As the purging fluid 98 is introduced through lumen 92 and flows in an annular space between the fiberscope and the lumen 92, the purging fluid may be forced to flow sideways into hood 12 through the one or more fluid apertures 94 while the distal opening of lumen 92 remains obstructed by the fiberscope. The purging fluid 98 forced through apertures 94 may flow 96 along the interior surface of hood 12 in a uniform manner, e.g., much like a "shower head", to uniformly purge blood (or other opaque fluids) from within the hood 12, consequently reducing the amount of saline required to establish visualization. Moreover, creating such a flow effect may prevent jets of the purging fluid from being purged distally in the event that fluid pressure and flow rate becomes too high as such jets of purging fluid may directly exit the hood aperture without thoroughly purging the hood 12.

Figure 11:
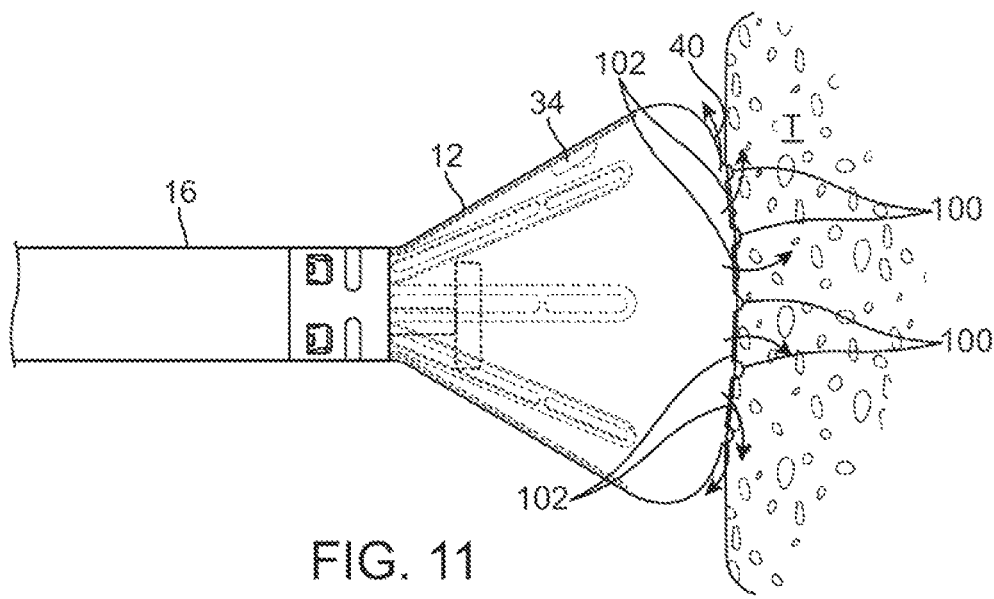
FIG. 11 shows a side view of another variation of the hood having a distal membrane which defines one or more projections which extend distally to actuate the opening of one or more corresponding valves.
Figure 12A:
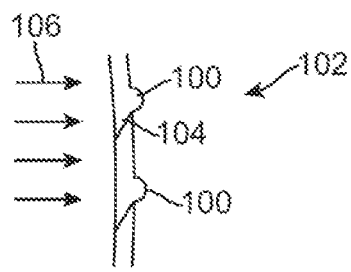
FIGS. 12A and 12B show detail side views of the one or more projections which actuate the opening of a corresponding valve when contacted against a tissue surface.
Figure 12B:
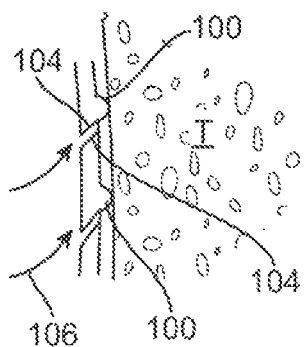

FIG. 11 shows yet another variation of a hood incorporating one or more protrusions or projections 100 extending from a distal membrane over hood 12. These protrusions or projections 100 may extend distally adjacent to a corresponding unidirectional valve 102 which has overlapping leaflets 104. The protrusions or projections 100 may comprise hemispherical protrusions made of a transparent elastomeric material (e.g., can be the same or different material as the imaging hood 12). In use, as hood 12 is filled with the purging fluid, flow through the valves 102 is inhibited or prevented by the overlapping leaflets 104, as shown in the cross-sectional detail view of FIG. 12A. As the distal face of the hood membrane 40 is pressed against a surface of tissue T to be visualized and/or treated, the protrusions or projections 100 pressing against the tissue surface may force the valve leaflets 104 to separate temporarily, thus allowing the passage of saline 106 out through the valves 102 to clear any blood within the hood 12 as well as any blood between membrane 40 and the tissue surface, as shown in the side view of FIG. 12B. Lifting hood 12 from the tissue may again allow the valve leaflets 104 to coapt and thus close the valve to prevent the blood from re-entering the hood 12 thus effectively reducing the amount of saline that is introduced into the patient's heart or bloodstream.

Figure 13:
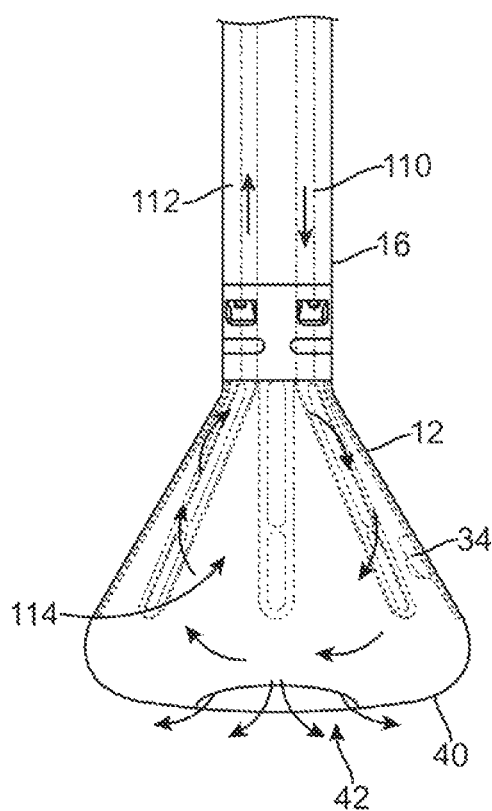
FIG. 13 shows a side view of another variation which incorporates a recirculating flow within the hood.

In yet another variation, FIG. 13 shows an imaging hood 12 which is configured to form a recirculating flow inside the hood 12. The purging fluid may be introduced (e.g., injected) as well as withdrawn from the imaging hood 12 interior through two different lumens in the catheter shaft 16. For instance, the fluid may be introduced by an inlet lumen 110 which injects the fluid along a first path into hood 12 while the recirculating fluid 114 may be withdrawn by suction through a separate outlet lumen 112. By keeping a relatively higher volume flow rate in inlet lumen 110 for injecting the purging fluid than the flow rate in outlet lumen 112 for withdrawing it, a considerable amount of purging fluid may be conserved resulting in efficient hood purging.

Figure 14:
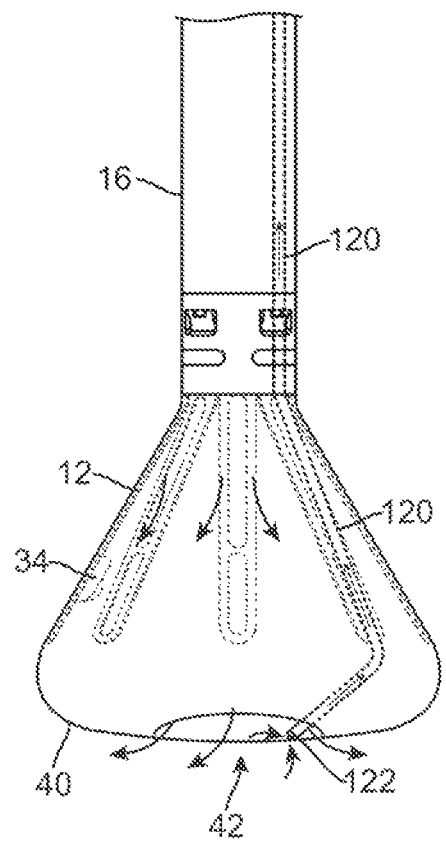
FIG. 14 shows a side view of another variation which incorporates a suction lumen for selective evacuation at or near the main aperture.

FIG. 14 shows a side view of another variation incorporating a suction lumen 120, e.g., a pre-bent lumen, extending from catheter 16 directly to the main aperture 42. This particular variation may allow for the direct evacuation of blood through a lumen opening 122 at a particular location along the main aperture 42 where the in-flow of blood (or other opaque fluids) is particularly high. For instance, when visualizing a pulmonary vein ostium in the left atrium of a patient's heart, the constant in-flow of blood into the imaging hood 12 from the pulmonary vein may occur. In order to overcome such a high in-flow rate, a higher flow rate or pressure of the purging fluid may be required to maintain visualization consequently increasing the amount of saline discharged into the patient's body. With the suction lumen 120, visualization can be achieved with a lower purging fluid flow rate or pressure when the suction lumen 120 is extended slightly out of the main aperture 42 or within the main aperture 42 to evacuate the in-flowing blood. The lumen opening 122 of suction lumen 120 can also be moved around the aperture space by torquing the suction lumen 120. The suction lumen 120 may also be used for evacuating any thrombosis or coagulated residue that may be formed during a therapeutic procedure, such as ablation.

Yet another variation is shown in the side view of FIG. 15 which illustrates a hood 12 partitioned into multiple chambers, e.g., chambers A, B, C, D, which are in fluid communication with individual corresponding fluid lumens defined through catheter 16. Each of the chambers A, B, C, D may be separated by corresponding transparent barriers 132, 134, 136 which extend along the length of hood 12. Although four chambers are shown in this example, fewer than four or greater than four chambers may be utilized. Each of the different chambers A, B, C, D may have a corresponding aperture 130A, 130B, 130C, 130D. The imaging element may be positioned inside the hood 12 to allow visualization of the tissue region.

Efficient purging and reduction of saline discharged may achieved when purging can be selectively stopped once a particular chamber establishes optical clarity. This can be done manually by the operator or through automation by a processor incorporated within the system. If automation is used, optical clarity of each individual chamber can be determined by quantifying the amount of red (co-related to amount of blood in chamber) through the Red:Green:Blue ratio of the image captured of a particular sector that corresponds to the particular chamber. FIG. 16 shows an example of a flow chart for the automated selective purging of individual chambers A, B, C, D. As all of the chambers A, B, C, D are initially purged 140, each chamber may be monitored as to whether it has obtained sufficient optical clarity 142A, 142B, 142C, 142D, i.e., whether a sufficient amount of blood (or other opaque bodily fluid) has cleared from the chamber to allow direct visualization of the underlying tissue region as detected either by the operator or automatically. If the respective chamber has not yet obtained sufficient optical clarity, the process of purging the chamber may be repeated or continued until sufficient optical clarity has been reached. Once the sufficient level of optical clarity has been reached, flow of the purging fluid into the respective chamber A, B, C, D may be stopped 144A, 144B, 144C, 144D. As different parts of the hood 12 may be cleared at different rates, flow of the purging fluid may be selectively stopped and/or continued in different chambers depending on the optical clarity and thus potentially reducing the amount of purging fluid released into the body.

Figure 17A:
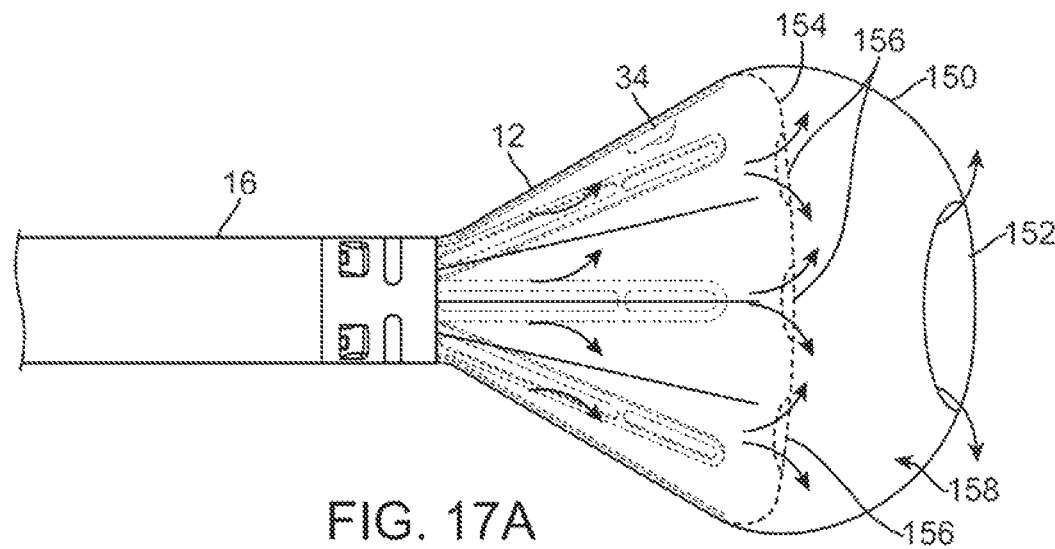
FIGS. 17A and 17B show side views of another variation which incorporates a distal chamber to facilitate the efficient purging of blood from the hood when contact against a tissue surface is at an angle.
Figure 17B:
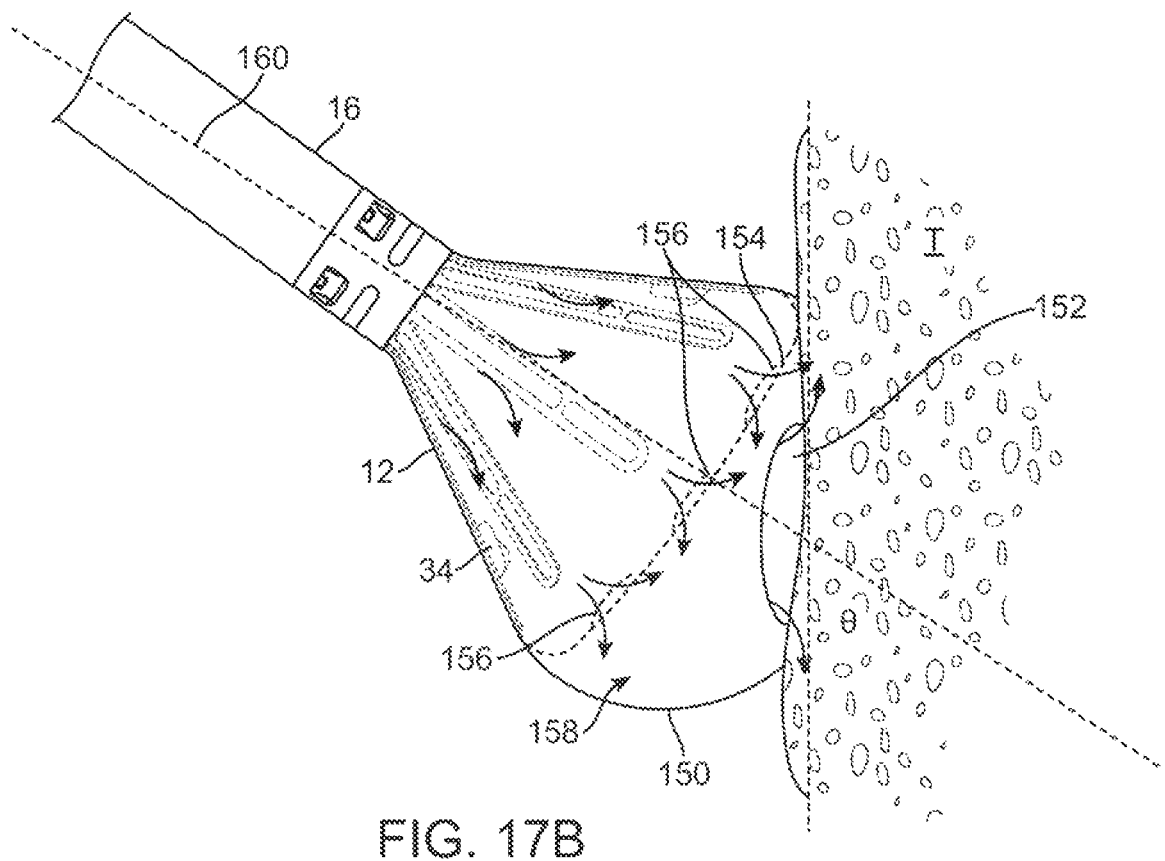

In yet another variation, FIGS. 17A and 17B show side views of a hood 12 which may incorporate an expandable distal membrane 150 which projects distally from hood 12 and is sufficiently soft to conform against the underlying contacted tissue. As shown, distal membrane 150 may define an intermediate chamber 158 between membrane 154 of hood 12 and the distal membrane 150. With membrane 154 defining one or more hood apertures 156, the purging fluid may enter within hood 12 and exit through hood apertures 156 into intermediate chamber 158 which may extend distally as shown in FIG. 17A. The purging fluid may exit intermediate chamber 158 through at least one central aperture 152. In the event that hood 12 contacts against a surface of tissue T at a non-perpendicular angle, as indicated by angle of incidence θ defined between the catheter longitudinal axis 160 and tissue surface, distal membrane 150 may conform to the tissue surface despite the angle of incidence θ. As result, distal membrane 150 may still establish contact with the tissue yielding a more efficient purging effect, as shown in FIG. 17B.

Figure 18:
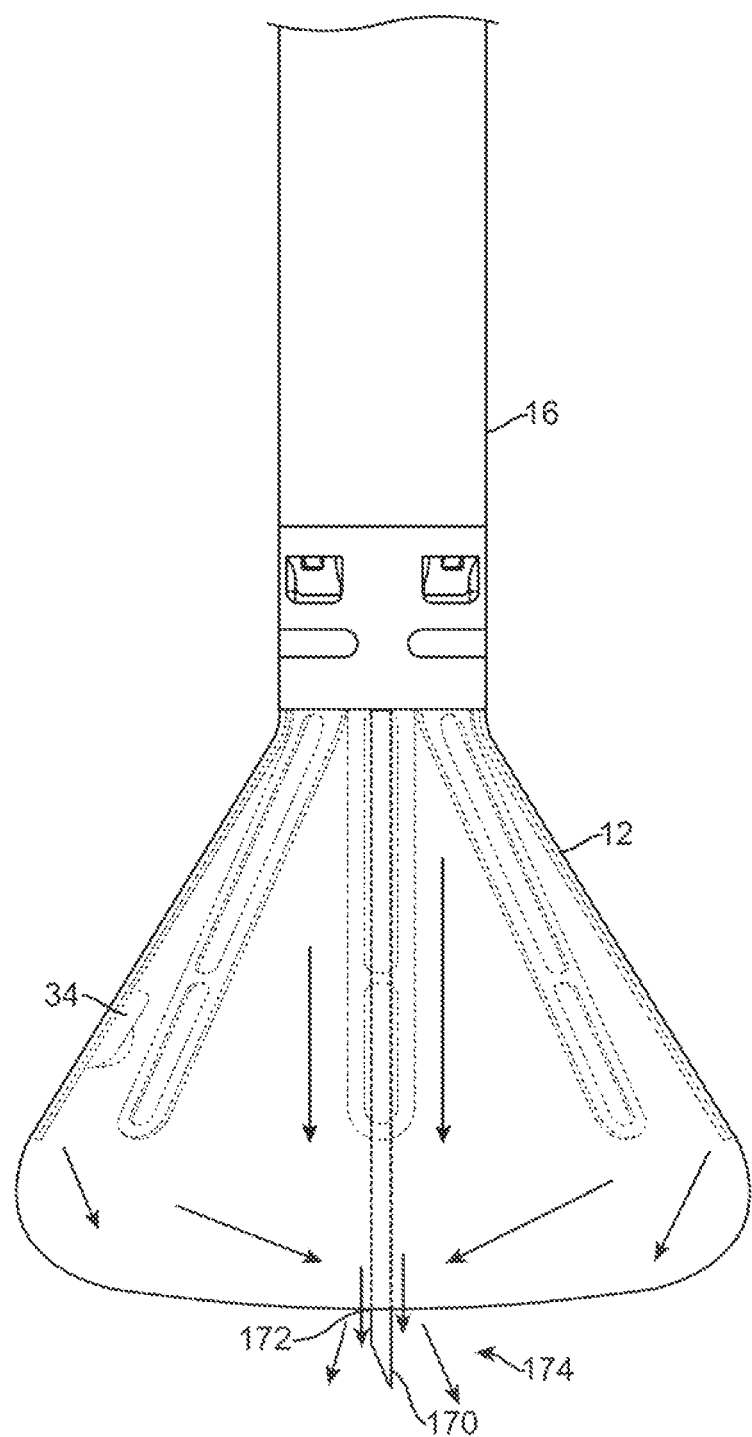
FIG. 18 shows a side view of another variation which comprises a piercing instrument, such as a needle, for forming an aperture through which the purging fluid may escape.

In yet another variation, as shown in the side view of FIG. 18, an imaging hood 12 may have distal membrane without an aperture and which may be filled with the purging fluid once desirably positioned within the subject's body in proximity to the tissue region to be visualized and/or treated. As the distal membrane is closed, the underlying tissue may be contacted and visualized through the hood 12. Once a tissue region to be treated has been located by hood 12, a piercing instrument, such as a transseptal or transmural needle 170, may be advanced through hood 12 from catheter 16 to puncture through the distal membrane at a desired site. This may form a puncture aperture 172 through which the purging fluid may escape 174. Hence, purging is only performed at locations where instruments are passed out of the imaging hood 12 thus reducing the amount of saline discharged out of the hood 12. A plurality of puncture apertures can be made across the distal membrane according to the needs of the procedure or the operator. Details of transseptal needles which may be utilized with apparatus and methods described herein are described in U.S. patent application Ser. No. 14/763,399 filed Jun. 14, 2007 (U.S. Pat. Pub. No. 2007/0293724 A1), which has been incorporated hereinabove. Details of transmural needles which may be utilized with apparatus and methods described herein are described in U.S. patent application Ser. No. 11/775,837 filed Jul. 10, 2007 (U.S. Pat. Pub. No. 2008/0009747 A1), which is incorporated herein by reference in its entirety.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method of inhibiting a flow of a purging fluid from a tissue visualization device, the method comprising:
    positioning an imaging hood attached to a distal end of a flexible elongate shaft in proximity to a tissue region to be visualized, the imaging hood including a distal membrane which defines a main aperture, wherein the imaging hood and the distal membrane define an open area;
    introducing the purging fluid into a proximal portion of the open area, the proximal portion bounded by a proximal membrane including a plurality of apertures;
    pressurizing the proximal membrane with the purging fluid to a partially extended state in which the purging fluid flows through the plurality of apertures and through the main aperture to an external environment; and
    pressurizing the proximal membrane with the purging fluid to a blocking extended state in which the proximal membrane obstructs the main aperture to block the flow of the purging fluid through the main aperture.

2. The method of claim 1 further comprising visualizing tissue underlying the hood via an imaging element positioned within or along the hood.

3. The method of claim 1 wherein the distal membrane is transparent.

4. The method of claim 1 wherein the proximal membrane is transparent.

5. The method of claim 1 wherein the flow of the purging fluid passes through the flexible elongate shaft.

6. The method of claim 1 wherein each aperture of the plurality of apertures has a diameter between 1 mm and 0.25 mm.

7. The method of claim 1 further comprising reducing a fluid pressure of the purging fluid on the proximal membrane to retract the proximal membrane from the main aperture.

8. The method of claim 1 wherein the proximal membrane is circumferentially attached to an inner wall of the imaging hood.

9. The method of claim 1 wherein the purging fluid is saline.

10. The method of claim 1 wherein the purging fluid flow into the external environment is greater when the proximal membrane is in the partially extended state than when the proximal membrane is in the blocking extended state.

* * * * *